United States Patent
Nakaya

(10) Patent No.: US 7,875,241 B2
(45) Date of Patent: Jan. 25, 2011

(54) SPECIMEN PREPARATION APPARATUS, SPECIMEN PREPARATION/ANALYSIS SYSTEM AND SPECIMEN PLATE

(75) Inventor: Masanori Nakaya, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 1547 days.

(21) Appl. No.: 11/172,035

(22) Filed: Jun. 30, 2005

(65) Prior Publication Data
US 2006/0029519 A1 Feb. 9, 2006

(30) Foreign Application Priority Data
Jun. 30, 2004 (JP) .............................. 2004-192880

(51) Int. Cl.
*G01N 21/00* (2006.01)

(52) U.S. Cl. .............................. 422/65; 422/63; 422/64; 422/66; 422/67; 435/287.1; 435/287.3; 436/46; 436/47; 436/48; 436/49

(58) Field of Classification Search ............. 422/63–67; 435/287.1, 287.3; 436/46–49
See application file for complete search history.

(56) References Cited

U.S. PATENT DOCUMENTS

| | | | |
|---|---|---|---|
| 5,311,426 A | | 5/1994 | Donohue et al. |
| 5,619,428 A | | 4/1997 | Lee et al. |
| 5,665,312 A | * | 9/1997 | Sperber et al. ................ 422/81 |
| 5,779,982 A | | 7/1998 | Aota et al. |
| 5,963,368 A | | 10/1999 | Domanik et al. |
| 6,268,208 B1 | | 7/2001 | Kondo |
| 6,319,470 B1 | | 11/2001 | Lefevre et al. |
| 6,329,139 B1 | | 12/2001 | Nova et al. |
| 6,352,861 B1 | | 3/2002 | Copeland et al. |
| 6,418,236 B1 | * | 7/2002 | Ellis et al. ................... 382/128 |
| 6,495,106 B1 | | 12/2002 | Kalra et al. |
| 6,562,299 B1 | * | 5/2003 | Ostgaard et al. .............. 422/65 |
| 6,916,659 B2 | * | 7/2005 | Gropp .......................... 436/50 |
| 2002/0074408 A1 | | 6/2002 | Torchalski |
| 2003/0022271 A1 | | 1/2003 | Voneiff et al. |
| 2003/0215936 A1 | | 11/2003 | Kallioniemi et al. |
| 2004/0052408 A1 | | 3/2004 | Sharman et al. |

(Continued)

FOREIGN PATENT DOCUMENTS

EP 0 740 142 B1 9/2001

(Continued)

OTHER PUBLICATIONS

Partial European Search Report for European Patent Application No. 05014030.0 dated Apr. 27, 2006 (7 pages).

(Continued)

*Primary Examiner*—Jyoti Nagpaul
(74) *Attorney, Agent, or Firm*—Brinks Hofer Gilson & Lione

(57) ABSTRACT

Provided is a specimen preparation apparatus capable of supplying a specimen from the specimen preparation apparatus to a specimen analyzer without burdening an operator. This specimen preparation apparatus comprises a stained specimen preparation part for preparing a specimen on a slide glass and staining the specimen, a keeping part for storing the stained specimen slide glass prepared in the stained specimen preparation part and a control part for deciding whether to supply the stained specimen slide glass to the keeping part or to the external apparatus.

9 Claims, 17 Drawing Sheets

U.S. PATENT DOCUMENTS

2004/0066960 A1 4/2004 McLaren et al.
2004/0072195 A1 4/2004 Hunkapiller et al.

FOREIGN PATENT DOCUMENTS

| | | |
|---|---|---|
| EP | 1 271 125 A2 | 1/2003 |
| EP | 1374987 A1 | 1/2004 |
| JP | H04-316169 | 6/1992 |
| JP | H04-291157 | 10/1992 |
| JP | H08-271390 A | 10/1996 |
| JP | 1020911 S | 9/1998 |
| JP | H11-237323 | 8/1999 |
| JP | 2000-075208 A | 3/2000 |
| WO | WO 92/09878 | 6/1992 |
| WO | WO 94/11720 A1 | 5/1994 |
| WO | WO 2004/001389 A1 | 12/2003 |

OTHER PUBLICATIONS

European Search Report for Application No. 05014030.0 dated Sep. 20, 2006.

Extended European Search Report for European Application No. 10158350.8, dated Jun. 30, 2010, 7 pages.

* cited by examiner

SPECIMEN PREPARATION APPARATUS, SPECIMEN PREPARATION/ANALYSIS SYSTEM AND SPECIMEN PLATE

This application claims priority under 35 U.S.C. §119 to Japanese Patent Application No. 2004-192880 filed Jun. 30, 2004, the entire content of which is hereby incorporated by reference.

BACKGROUND OF THE INVENTION

1. Field of the Invention

The present invention relates to a specimen preparation apparatus, a specimen preparation/analysis system and a specimen plate, and more particularly, it relates to a specimen preparation apparatus for preparing a specimen on a slide glass, a specimen preparation/analysis system and a specimen plate having a specimen preparation area for preparing a specimen.

2. Description of the Background Art

A blood smear A blood smear preparation apparatus preparing a blood specimen by smearing blood on a slide glass (specimen plate) is generally known as a specimen preparation apparatus, as disclosed in U.S. Pat. No. 5,779,982, for example. The aforementioned U.S. Pat. No. 5,779,982 discloses a blood smear preparation apparatus automatically carrying out steps from that of smearing blood on a slide glass up to a staining step. In the blood smear preparation apparatus disclosed in U.S. Pat. No. 5,779,982, cassettes storing stained slide glasses (specimens) respectively are kept in a keeping part provided in the blood smear preparation apparatus.

On the other hand, an automatic blood cell analyzer automatically classifying blood cells by digitally image-processing a blood specimen is generally known as a specimen analyzer. A smear prepared in the aforementioned blood smear preparation apparatus can be analyzed with this automatic blood cell analyzer. In order to analyze the smear prepared in the blood smear preparation apparatus with the automatic blood cell analyzer, an operator generally unloads a stained slide glass (specimen) stored in the corresponding cassette kept in the keeping part of the blood smear preparation apparatus, stores the slide glass in a magazine dedicated to the automatic blood cell analyzer and sets the magazine on the automatic blood cell analyzer.

According to the aforementioned conventional method requiring the operator to unload the stained slide glass (specimen) from the cassette kept in the blood smear preparation apparatus, store the same in the magazine and set the magazine on the automatic blood cell analyzer, however, the operator is disadvantageously burdened.

SUMMARY OF THE INVENTION

The present invention The present invention has been proposed in order to solve the aforementioned problem, and an object thereof is to provide a specimen preparation apparatus capable of supplying a specimen from the specimen preparation apparatus to a specimen analyzer without burdening an operator and a specimen preparation/analysis system.

Another object of the present invention is to provide a specimen plate allowing the operator to confirm a large quantity of detailed specimen information without inquiring specimen information from a host computer.

In order to attain the aforementioned objects, a specimen preparation apparatus according to a first aspect of the present invention, which is a specimen preparation apparatus capable of preparing a specimen on a slide glass, staining the specimen and supplying the stained specimen slide glass formed with the stained specimen to an external apparatus, comprises a stained specimen preparation part for preparing the specimen on the slide glass and staining the specimen, a keeping part for storing the stained specimen slide glass prepared in the stained specimen preparation part and a control part for deciding whether to supply the stained specimen slide glass to the keeping part or to the external apparatus.

A specimen preparation/analysis system according to a second aspect of the present invention comprises specimen preparation means for preparing a stained specimen slide glass by preparing a specimen on a slide glass and staining the specimen, specimen analysis means for analyzing the stained specimen slide glass and specimen keeping/supply means having a first keeping part for keeping the stained specimen slide glass prepared in the specimen preparation means and a supply part for supplying the stained specimen slide glass to the specimen analysis means.

A specimen preparation/analysis system according to a third aspect of the present invention comprises a specimen preparation apparatus for preparing a stained specimen slide glass by preparing a specimen on a slide glass and staining the specimen and a sample analyzer including analysis means for analyzing the stained specimen slide glass prepared in the specimen preparation apparatus, identification information detection means detecting identification information provided in the stained specimen slide glass and analysis control means controlling the analysis means on the basis of the detected identification information.

A specimen plate according to a fourth aspect of the present invention comprises a specimen preparation area for preparing a specimen and an information display area for displaying specimen-related information. The information display area includes a first display area displaying a bar code bidirectionally holding the specimen-related information in horizontal and vertical directions in plan view and a second display area displaying the specimen-related information in a visually recognizable format.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is now described with reference to the drawings.

First, the overall structure of a specimen preparation/analysis system according to this embodiment is described with reference to FIGS. 1 to 3.

Figure 1:
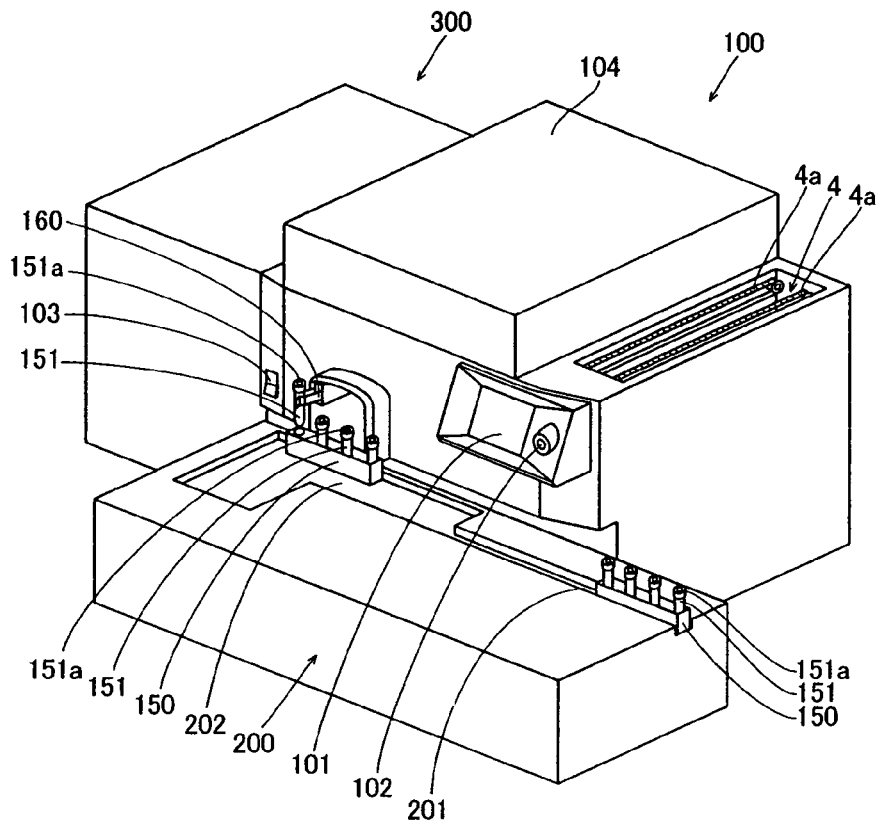
FIG. 1 is a perspective view showing the overall structure of a specimen preparation/analysis system according to an embodiment of the present invention.

As shown in FIG. 1, the specimen preparation/analysis system according to this embodiment comprises a blood smear preparation apparatus 100, a transporter 200 and an automatic blood cell analyzer 300. The automatic blood cell analyzer 300 digitally image-processes a specimen prepared in the blood smear preparation apparatus 100 while automatically classifying blood cells. The blood smear preparation apparatus 100 prepares two types of specimens, i.e., an automatically analyzed specimen analyzable in the automatic blood cell analyzer 300 and a visually observed specimen allowing visual analysis. The transporter 200 is set on the front surface of the blood smear preparation apparatus 100, while the automatic blood cell analyzer 300 is set on a side surface of the blood smear preparation apparatus 100. A host computer 400 is connected to a control part 110 of the blood smear preparation apparatus 100, as shown in FIG. 2.

As shown in FIG. 1, the transporter 200 is provided for automatically transporting a sample rack 150 storing test tubes 151 storing blood to the blood smear preparation apparatus 100. The blood smear preparation apparatus 100 includes a display operation part 101 formed by a touch panel, a starting switch 102, a power switch 103 and a cover 104. The blood smear preparation apparatus 100 is further provided with a hand member 160 for transporting the test tubes 151 storing blood from the transporter 200 toward the blood smear preparation apparatus 100. Rubber stoppers 151a are attached to the test tubes 151 storing blood.

Figure 3:
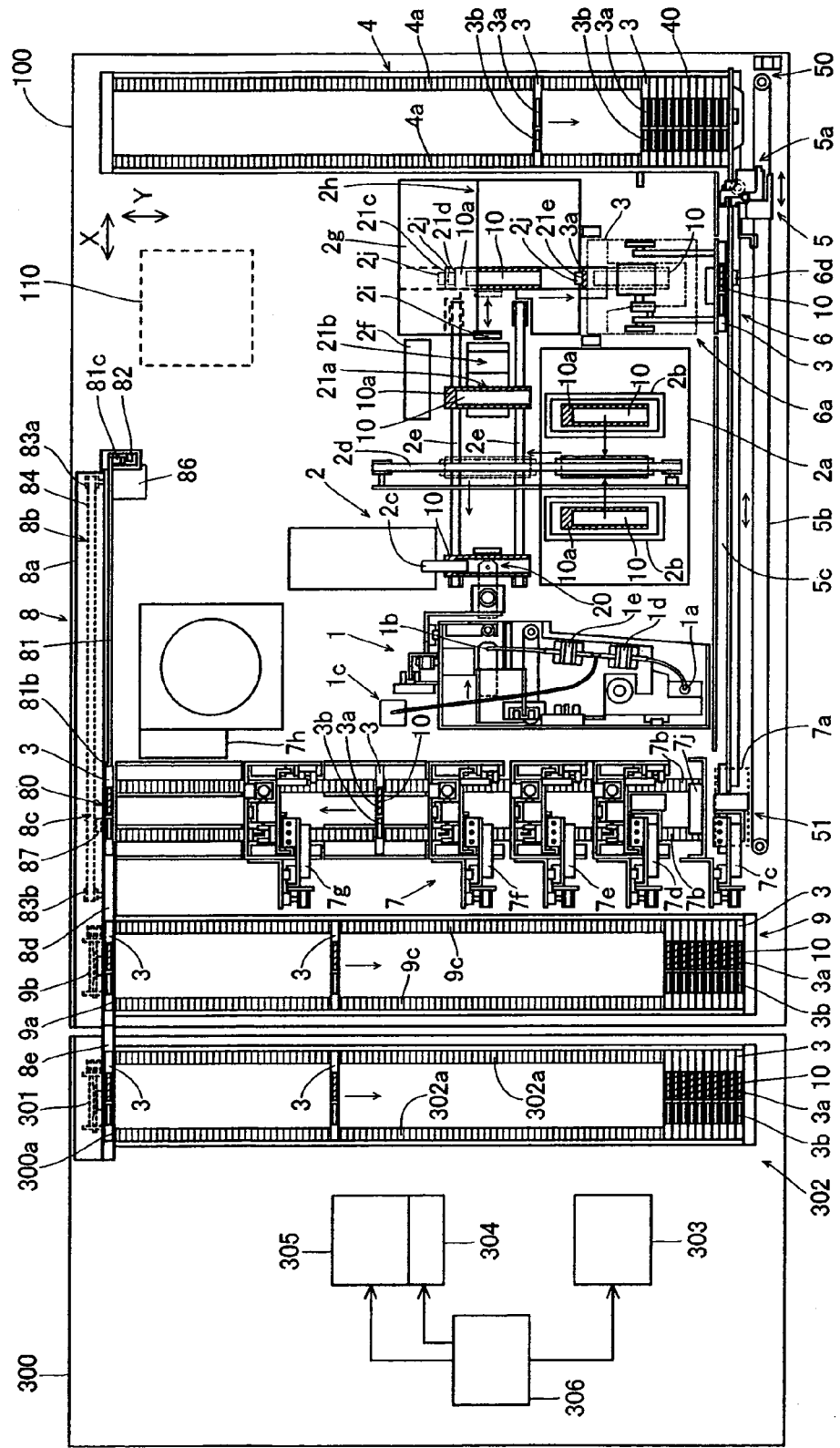
FIG. 3 is a plan view of the internal structure of the specimen preparation/analysis system according to the embodiment shown in FIG. 1.

As shown in FIG. 3, the blood smear preparation apparatus 100 comprises a sucking/dispensing mechanism part 1, a smearing part 2, resin cassettes 3, a cassette storage part 4, a first cassette transport part 5, a slide glass insertion part 6, a staining part 7, a second cassette transport part 8 and a keeping part 9. The sucking/dispensing mechanism part 1 has a function of sucking blood from each test tube 151 transported toward the blood smear preparation apparatus 100 by the hand member 160 (see FIG. 1) while dropping the sucked blood on slide glasses 10. As shown in FIG. 3, this sucking/dispensing mechanism part 1 includes a piercer (suction needle) 1a for sucking the blood from each test tube 151, a pipette 1b for dispensing the sucked blood to the slide glasses 10, a syringe pump 1c connected to the piercer 1a and the pipette 1b, a valve 1d for opening/closing a passage between the piercer 1a and the syringe pump 1c and another valve 1e for opening/closing another passage between the pipette 1b an the syringe pump 1c.

According to this embodiment, the sucking/dispensing mechanism part 1 has a function of dispensing the same blood (sample) to two slide glasses 10 while regulating the volume of the dispensed blood to those corresponding to an automatically analyzed specimen and a visually observed specimen respectively.

The smearing part 2 is provided for supplying the slide glasses 10 to a dispensing/smearing position 20 while smearing the slide glasses 10 with the dropped blood, drying the same and printing information on the slide glasses 10. This smearing part 2 is provided with a slide glass supply part 2a, two slide glass storage parts 2b, a draw glass 2c, feeding belts 2d and 2e, a fan 2f, a printing part 2g and a slide glass transport part 2h.

The slide glass supply part 2a has a function of supplying the slide glasses 10 stored in the two slide glass storage parts 2b onto the feeding belts 2e with an unloading mechanism (not shown) and chucks (not shown) mounted on the feeding belt 2d. The feeding belts 2e are so formed as to transport the slide glasses 10 to the dispensing/smearing position 20 and drying positions 21a and 21b. The draw glass 2c is rendered movable to a position for coming into contact with the slide glasses 10 and also movable along the longitudinal direction of the slide glasses 10, to be capable of smearing the slide glasses 10 with the blood dispensed thereto on the dispensing/smearing position 20. The fan 2f is provided for drying the blood smeared on the slide glasses 10 transported to the drying positions 21a and 21b.

Figure 4:
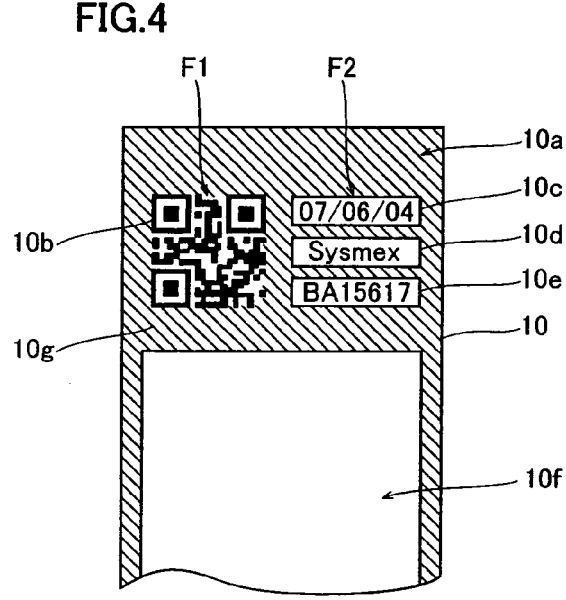
FIG. 4 is an enlarged view of a frosted part of a slide glass employed in the specimen preparation/analysis system according to the embodiment shown in FIG. 1.

According to this embodiment, the printing part 2g is formed by a thermal transfer printer. This printing part 2g is provided for printing a two-dimensional bar code 10b storing specimen information such as a sample number, a date, a serial number and a name and three rows of text data formed by the date (Jul. 6, 2004) 10c, the name (Sysmex) 10d and the sample number (BA 15617) 10e included in the specimen information as attribute information on a frosted part (information display area) 10a of each slide glass 10, as shown in FIG. 4. The term "two-dimensional bar code" denotes a bar code bidirectionally holding information in horizontal and vertical directions in plan view. The two-dimensional bar code 10b printed on the frosted part 10a of the slide glass 10 is formed by a data matrix or a QR code. The quantity of information (the number of storable characters) in the two-dimensional bar code 10b is 50 digits at the maximum for half-sized characters, or 25 digits at the maximum for full-sized characters.

Durable ink is employed for the printing part (thermal transfer printer) 2g, so that the two-dimensional bar code 10b and the text data (10c to 10e) printed on the frosted part 10a of the slide glass 10 are not eluted by an organic solvent such as alcohol or xylene employed in staining and microscopy.

Figure 5:
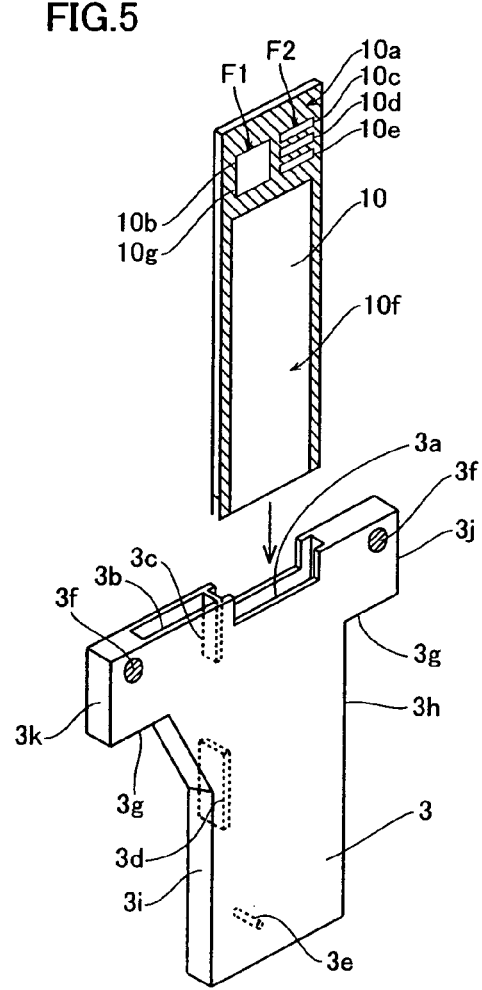
FIGS. 5 and 6 are perspective views of a cassette and the slide glass employed in the specimen preparation/analysis system according to the embodiment shown in FIG. 1.

According to this embodiment, the frosted part (information display area) 10a of the slide glass 10 is arranged on a region closer to one end of the slide glass 10 to be adjacent to a specimen preparation area 10f along the longitudinal direction of the slide glass 10, as shown in FIGS. 4 and 5. A bar code print area F1 and a text print area F2 of the frosted part 10a printed with the two-dimensional bar code 10b and the three rows of text data (10c to 10e) respectively are arranged to be adjacent to each other along the shorter direction of the slide glass 10. The two-dimensional bar code 10b has a square shape in plan view. The three rows of text data (10c to 10e) are arranged to be adjacent to each other at prescribed intervals along the longitudinal direction of the slide glass 10, so that the lengths of the bar code print area F1 and the text print area F2 are equal to each other along the longitudinal direction of the slide glass 10. The characters and numerals constituting the three rows of text data (10c to 10e) respectively are arranged along the shorter direction of the slide glass 10. In this case, eight half-sized characters are printable as the text data at the maximum.

According to this embodiment, a printable coating film 10g of a coating agent such as resin is formed on a region of the slide glass 10 corresponding to the frosted part 10a. The coating agent constituting this coating film 10g has excellent durability against the organic solvent such as alcohol or xylene employed in staining and microscopy. The two-dimensional bar code 10b and the three rows of text data (10c to 10e) are printed on the upper surface of the coating film 10g located on the frosted part 10a. The coating film 10g is formed to extend from the frosted part 10a along the longitudinal direction of the slide glass 10 for holding the specimen preparation area 10f.

As shown in FIG. 3, the slide glass transport part 2h is provided for moving the slide glasses 10 from ends of the feeding belts 2e to the printing part 2g while moving the printed slide glasses 10 to storage positions of the cassettes 3. This slide glass transport part 2h includes a transverse mover 2i for transversely moving the slide glasses 10 from the ends of the feeding belts 2e to a transverse printing position 21c along allow X in FIG. 3 and a vertical mover 2j for vertically moving the slide glasses 10 to a vertical printing position 21d and a storage position 21e for the cassettes 3 along arrow Y in FIG. 3 respectively.

Figure 6:
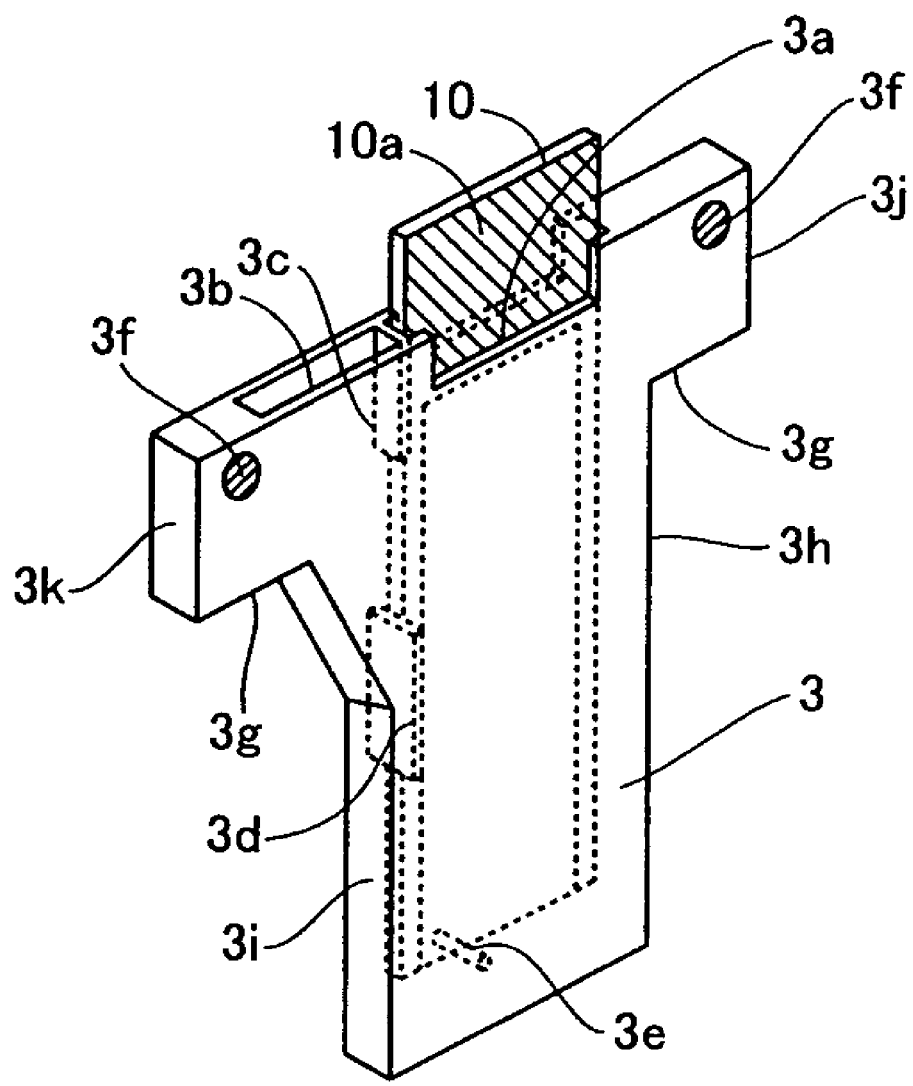

As shown in FIGS. 5 and 6, each resin cassette 3 is rendered capable of storing each smeared slide glass 10 and a liquid (stain) employed in a staining step. More specifically, the cassette 3 includes a slide glass receiving hole 3a, a stain sucking/dispensing hole 3b, partitions 3c and 3d, a slide glass support part 3e, two magnet adsorption members 3f of a metal for adsorbing magnets, a transport belt engaging part 3g, a pair of side face parts 3h and 3i and another pair of side face parts 3j and 3k. The slide glass receiving hole 3a and the stain sucking/dispensing hole 3b communicate with each other inside the cassette 3. The side face parts 3j and 3k project beyond the side face parts 3h and 3i by a prescribed amount respectively, and are arranged on upper portions of the cassette 3.

As shown in FIG. 3, the cassette storage part 4, provided for introducing the cassettes 3 into the apparatus, includes a feeding belt 4a.

The first cassette transport part 5 shown in FIG. 3 is provided for transporting the cassettes 3 received from the cassette storage part 4 to the slide glass insertion part 6 and the staining part 7. This first cassette transport part 5 includes a horizontally movable cassette transport member 5a, a driving belt 5b for horizontally moving the cassette transport member 5a and a transport path 5c for transporting the cassettes 3 supplied from the cassette storage part 4.

The slide glass insertion part 6 shown in FIG. 3 is provided for storing the smeared and printed slide glasses 10 into the slide glass receiving holes 3a of the cassettes 3. This slide glass insertion part 6 includes a cassette rotation mechanism part 6a for horizontally arranging the cassettes 3 to be capable of receiving the slide glasses 10.

The staining part 7 shown in FIG. 3 is provided for staining the smeared slide glasses 10 by supplying the stain to the stain sucking/dispensing holes 3b of the cassettes 3 transported by the cassette transport member 5a. This staining part 7 includes a feed member 7a for feeding the cassettes 3 transported by the cassette transport member 5a into a second sucking/discharging part 7d of the staining part 7, transport belts 7b for transporting the cassettes 3 received from the feed member 7a, first to fifth sucking/discharging parts 7c to 7g for supplying and discharging the stain to and from the cassettes 3 and a fan 7h for drying the smeared slide glasses 10.

Figure 7:
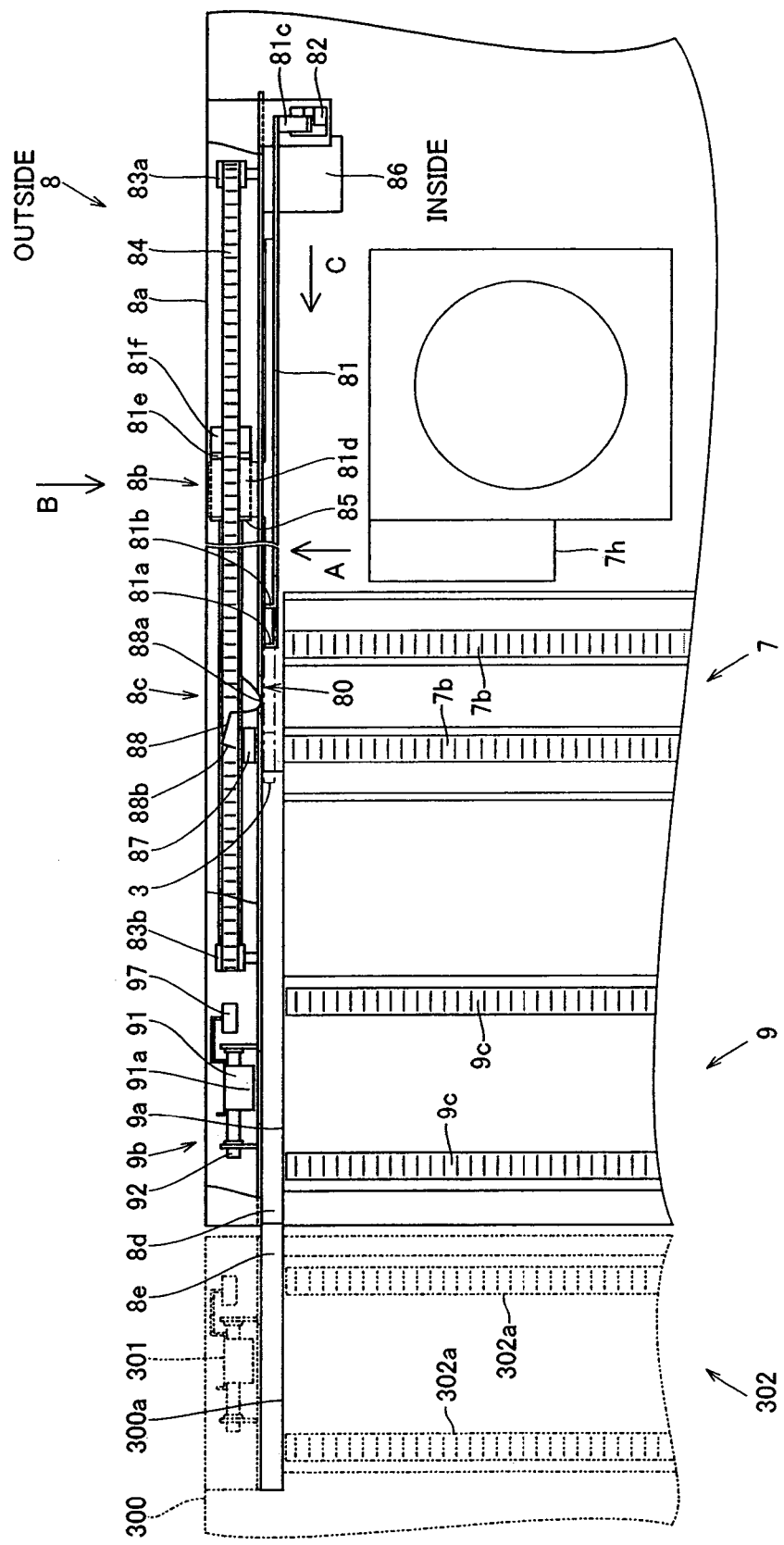
FIG. 7 is a top plan view of a second cassette transport part of a specimen preparation apparatus of the specimen preparation/analysis system according to the embodiment shown in FIG. 1.
Figure 8:
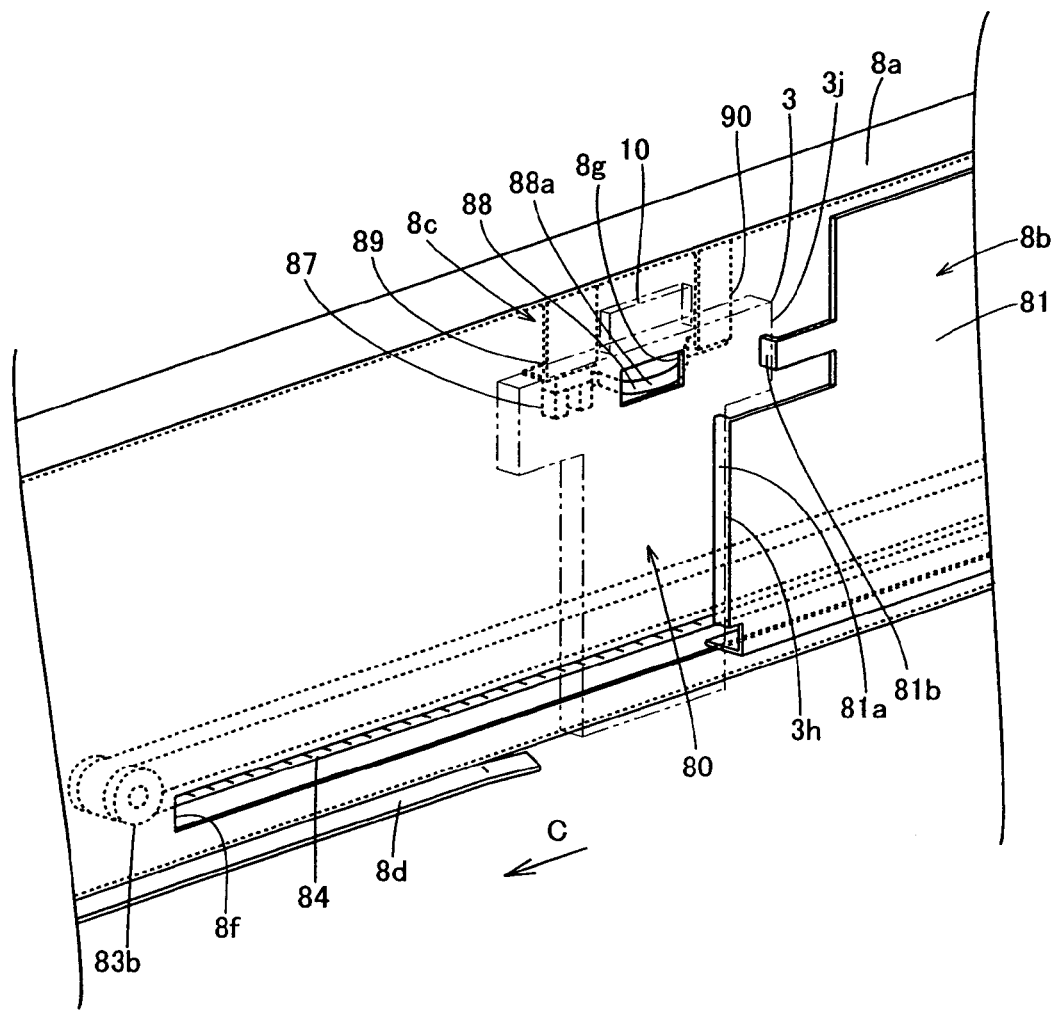
FIG. 8 is a perspective view of the second cassette transport part shown in FIG. 7 as viewed from a direction A.
Figure 10:
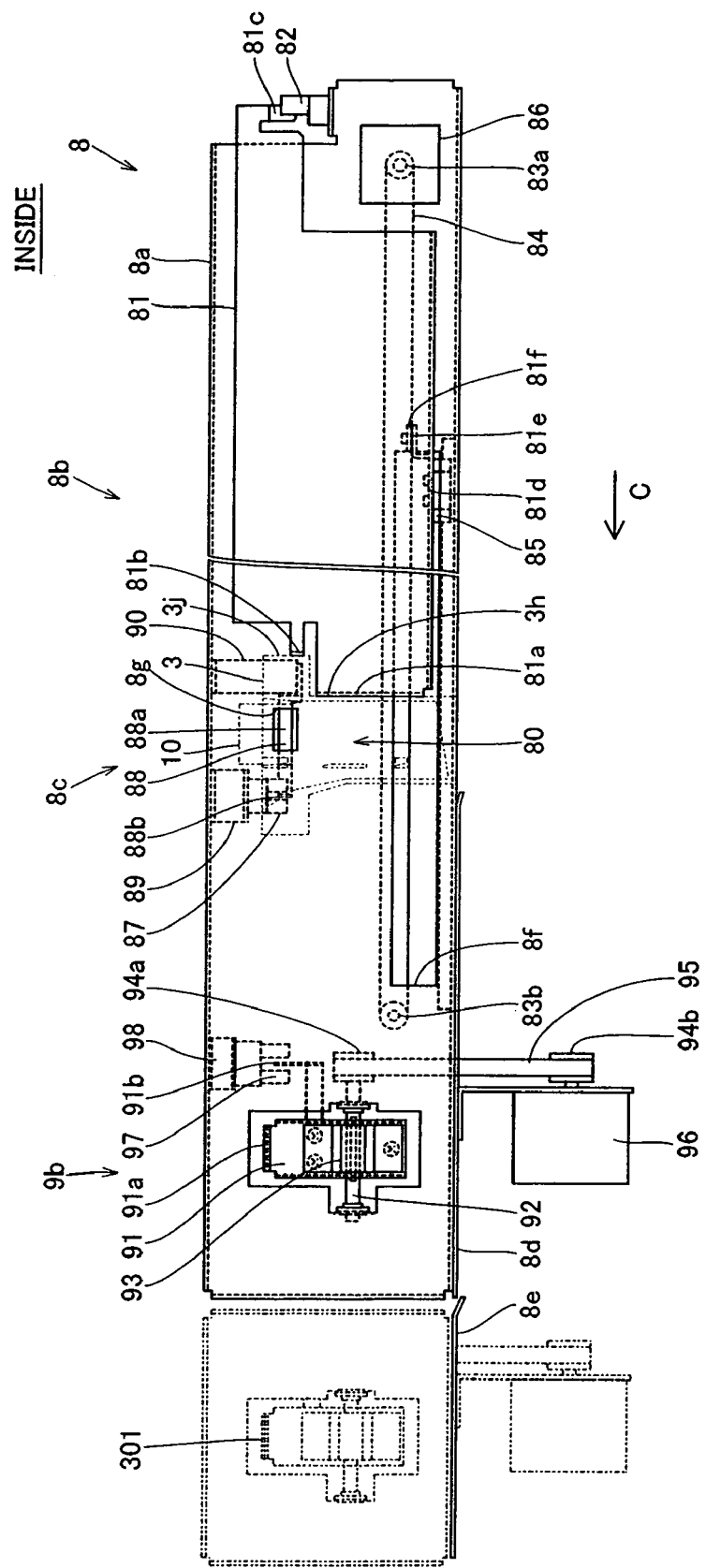
FIG. 10 is a plan view of the second cassette transport part shown in FIG. 7 as viewed from the direction A.
Figure 11:
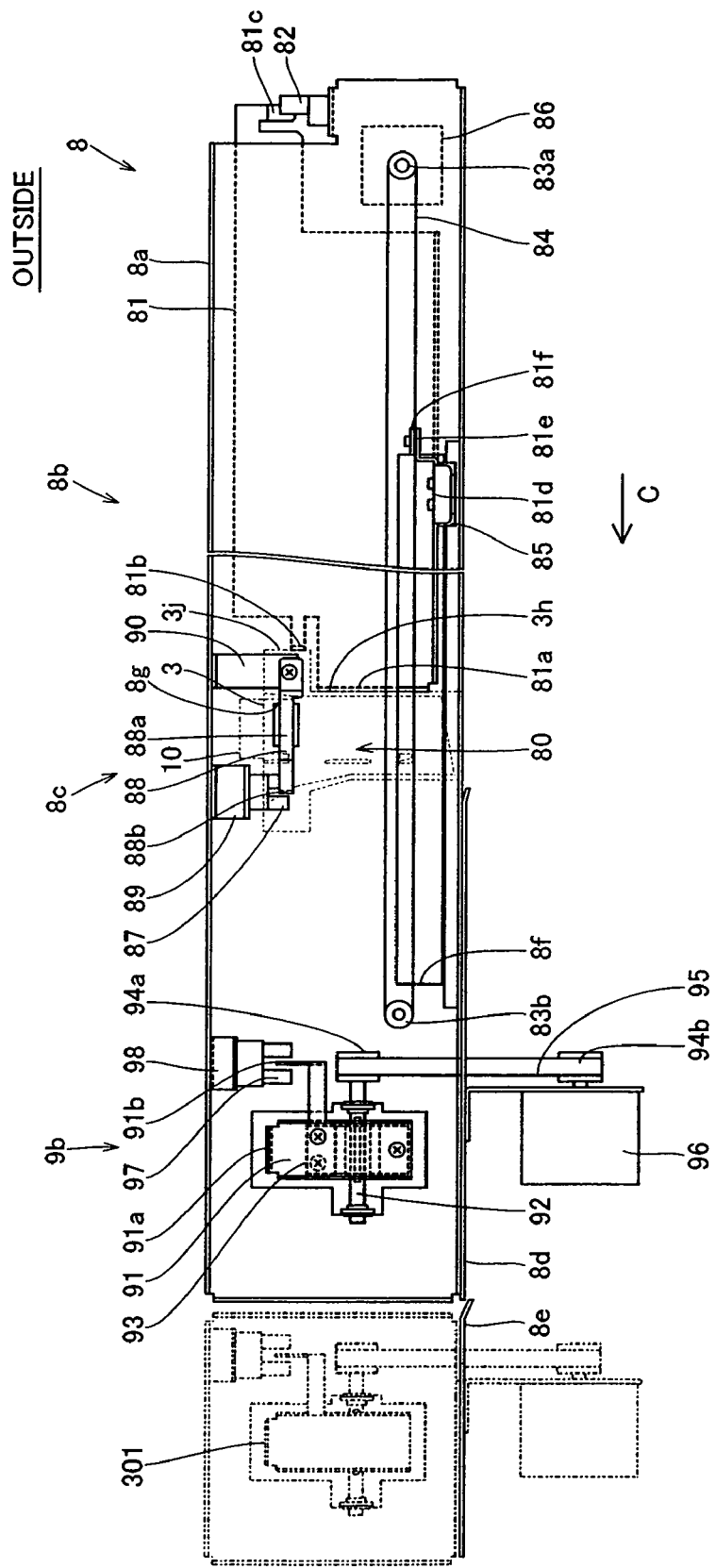
FIG. 11 is another plan view of the second cassette transport part shown in FIG. 7 as viewed from the direction B.

According to this embodiment, the second cassette transport part 8 is rendered capable of transporting the cassettes 3 storing the smeared slide glasses 10 to both of an inlet 300a of the automatic blood cell analyzer 300 and a port 9a of the keeping part 9 of the blood smear preparation apparatus 100. The structure of the second cassette transport part 8 according to this embodiment is now described in detail with reference to FIGS. 3 and 7 to 13. As shown in FIG. 7, the second cassette transport part 8 is constituted of a transport part 8b mounted on a frame 8a, a cassette detection part 8c and transport paths 8d and 8e. As shown in FIGS. 8, 10 and 11, the frame 8a is provided with holes 8f and 8g in a lower region corresponding to the transport part 8b and a region corresponding to the cassette detection part 8c respectively.

Figure 9:
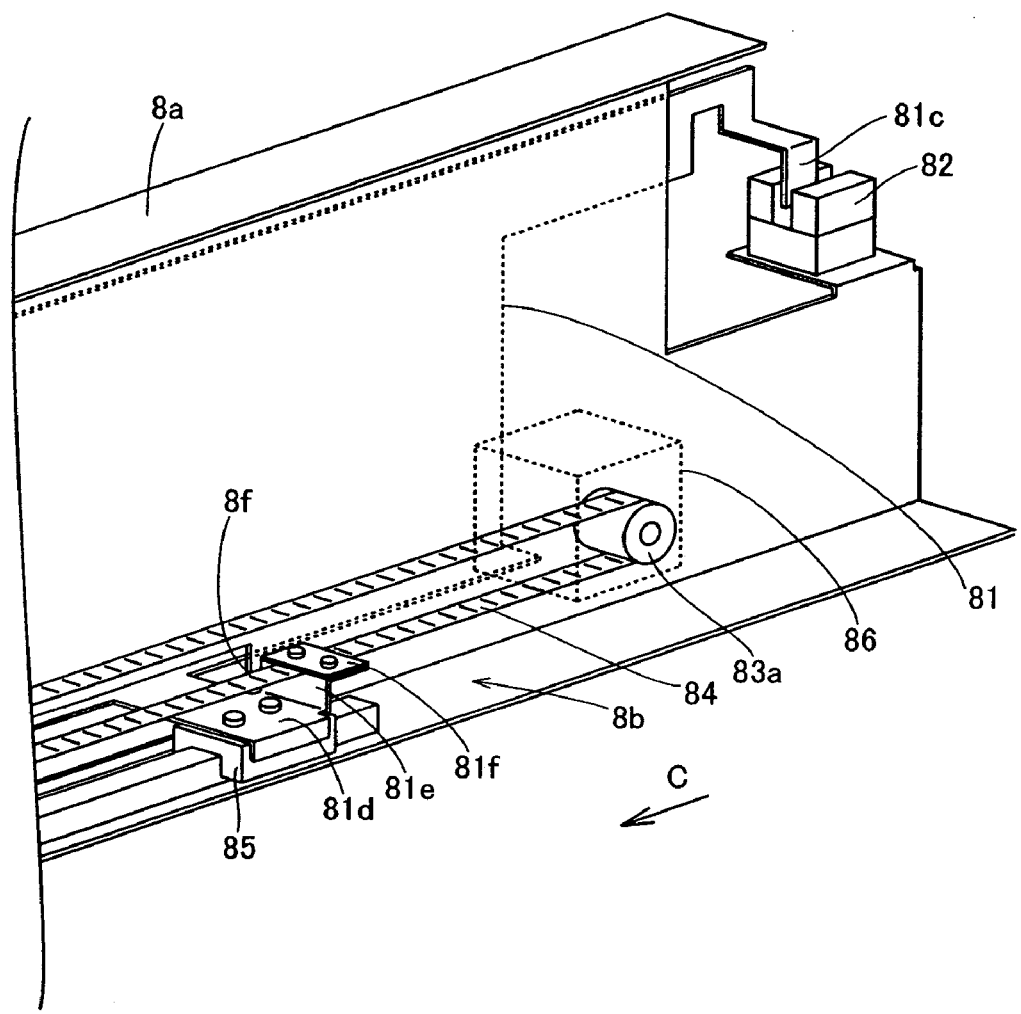
FIG. 9 is another perspective view of the second cassette transport part shown in FIG. 7 as viewed from a direction B.

As shown in FIGS. 7 and 9, the transport part 8b is constituted of a moving member 81, a moving member sensor 82, pulleys 83a and 83b, a driving belt 84, a direct-acting guide 85 and a drive motor 86. As shown in FIG. 7, the moving member sensor 82 and the drive motor 86 are arranged inside the frame 8a, while the pulleys 83a and 83b, the driving belt 84 and the direct-acting guide 85 are arranged outside the frame 8a.

As shown in FIGS. 7 to 9, the moving member 81 is made of sheet metal, and has two contact parts 81a and 81b, a detection part 81c and a mounting part 81d. The two contact parts 81a and 81b and the detection part 81c of the moving member 81 are arranged inside the frame 8a as shown in FIGS. 7 and 10, while the mounting part 81d is arrange outside the frame 8a through the hole 8f of the frame 8a as shown in FIGS. 7 and 11.

The contact parts 81a and 81b of the moving member 81 come into contact with the side face parts 3h and 3j of each cassette 3 respectively for moving the cassette 3, as shown in FIG. 8. As shown in FIG. 9, the detection part 81c of the moving member 81 is provided for detecting the position of the moving member 81 with the moving member sensor 82. The mounting part 81d of the moving member 81 is mounted on the direct-acting guide 85. A belt coupling part 81e is provided on the mounting part 81d of the moving member 81. This belt coupling part 81e is coupled to the driving belt 84 with a mounter 81f. As shown in FIG. 7, the driving belt 84 is mounted on the pulleys 83a and 83b, while the pulley 83a is coupled to the drive motor 86. Thus, the drive motor 86 rotates the pulley 83a while driving the driving belt 84, thereby moving the moving member 81 coupled to the driving belt 84. The interval between the pulleys 83a and 83b mounted with the driving belt 84 is so set that the contact parts 81a and 81b of the moving member 81 coupled to the driving belt 84 can reach the inlet 300a of the automatic blood cell analyzer 300.

Figure 12:
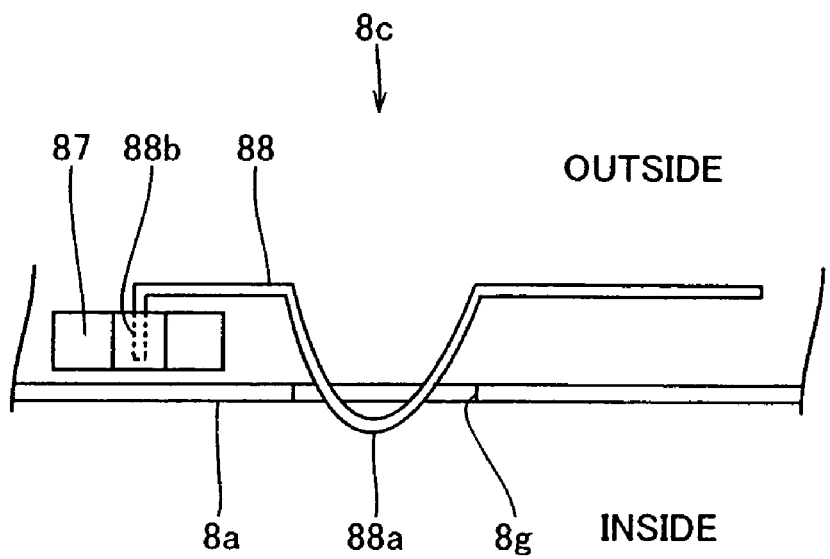
FIGS. 12 and 13 are enlarged views of a cassette detection part of the second cassette transport part shown in FIG. 7.
Figure 13:
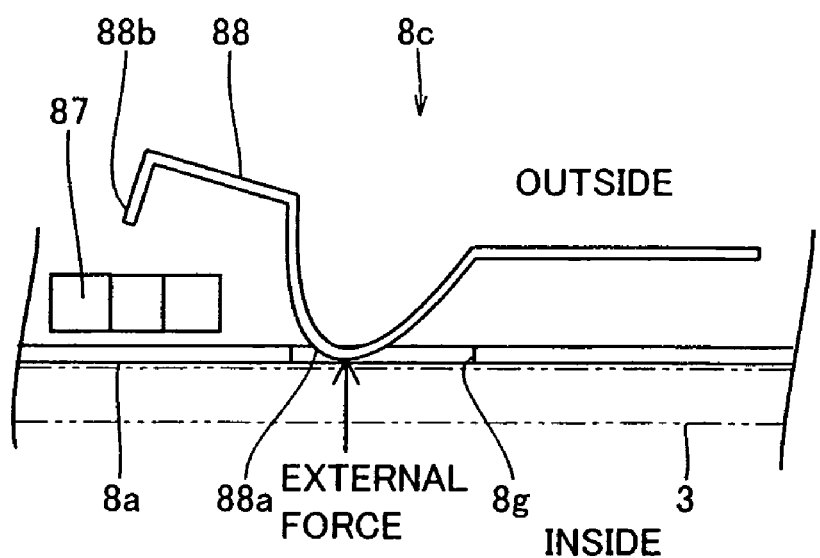

As shown in FIG. 11, the cassette detection part 8c is arranged outside the frame 8a. This cassette detection part 8c is set on a region, receiving each cassette 3 transported from the staining part 7 (see FIG. 3), forming a transport starting position 80. The cassette detection part 8c is constituted of a cassette sensor 87, a detector 88 and two brackets 89 and 90. As shown in FIG. 12, the detector 88 has a plate spring structure formed by a bent part 88a and a detection part 88b. The bent part 88a of the detector 88 is so arranged that its projecting portion projects into the frame 8a through the hole 8g thereof. When external force is applied to the bent part 88a of the detector 88 from the inside of the frame 8a, the bent part 88a and the detection part 88b of the detector 88 are moved toward the outside of the frame 8a, as shown in FIG. 13. The cassette sensor 87 has a function of sensing the detection part 88b of the detector 88, as shown in FIGS. 12 and 13. The cassette sensor 87 and the detector 88 are mounted on the frame 8a through the brackets 89 and 90 respectively, as shown in FIG. 11.

As shown in FIG. 7, the transport paths 8d and 8e are made of sheet metal. An end of the transport path 8d is arranged on a region corresponding to the transport starting position 80, while the other end thereof is arranged on a prescribed region in the blood smear preparation apparatus 100 adjacent to the inlet 300a (see FIG. 3) of the automatic blood cell analyzer 300. The transport part 8e is arranged on the inlet 300a of the automatic blood cell analyzer 300. The transport paths 8d and 8e serve as passages for the cassettes 3 pushed and moved by the moving member 81.

The keeping part 9 shown in FIG. 3 is provided for keeping the cassettes 3 storing the slide glasses 10 stained in the staining part 7. The stained slide glasses (specimens) 10 introduced into the keeping part 9 are visually analyzed. This keeping part 9 is provided with a feed part 9b and a transport belt 9c.

According to this embodiment, the feed part 9b is mounted on the frame 8a of the second cassette transport part 8 and arranged on a region corresponding to the port 9a of the keeping part 9, as shown in FIG. 7. This feed part 9b is provided for moving the cassettes 3 transported to the port 9a of the keeping part 9 by the second cassette transport part 8 toward the keeping part 9.

Figure 16:
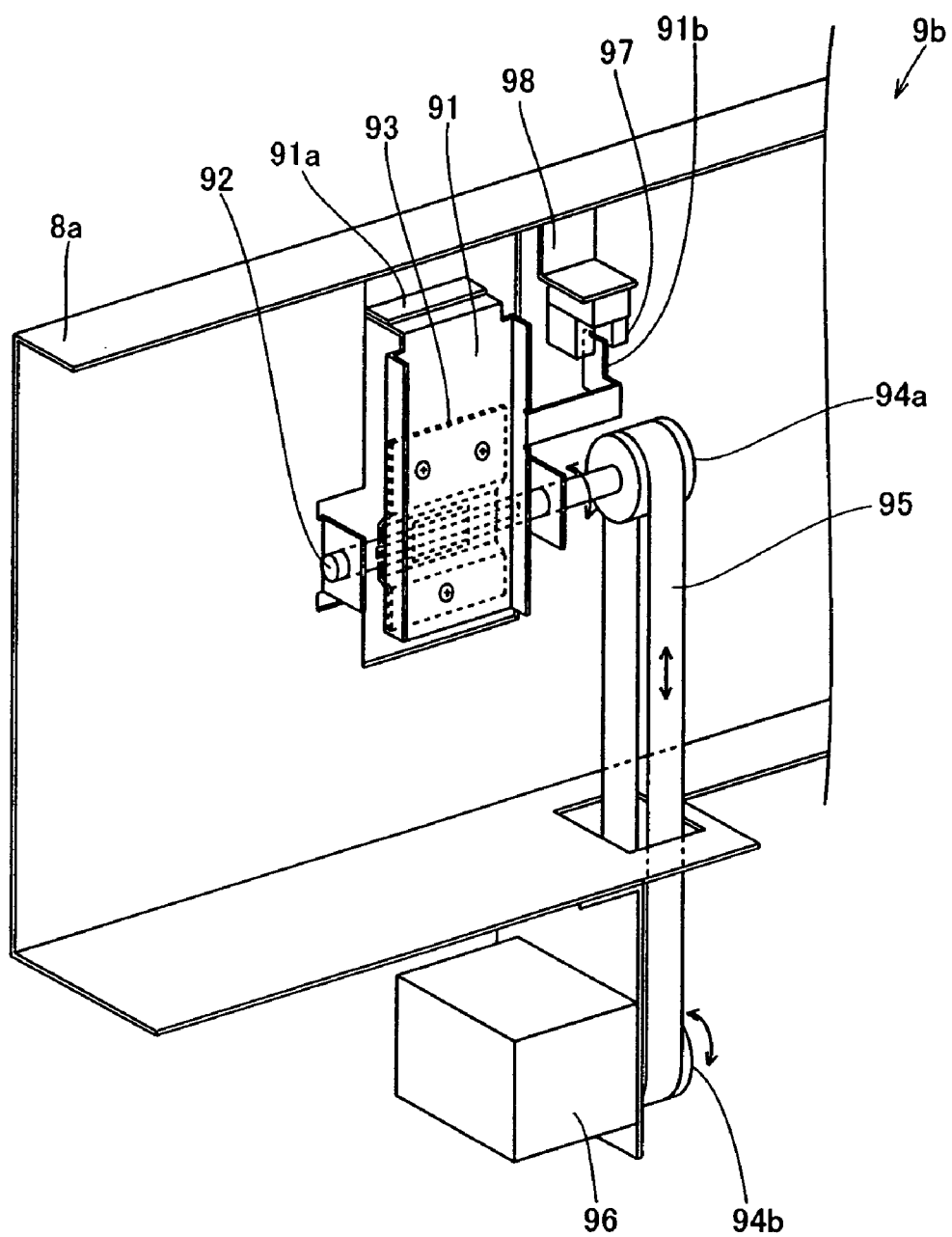
FIG. 16 is a perspective view of a feed part of a keeping part of the specimen preparation apparatus of the specimen preparation/analysis system according to the embodiment shown in FIG. 1.
Figure 17:
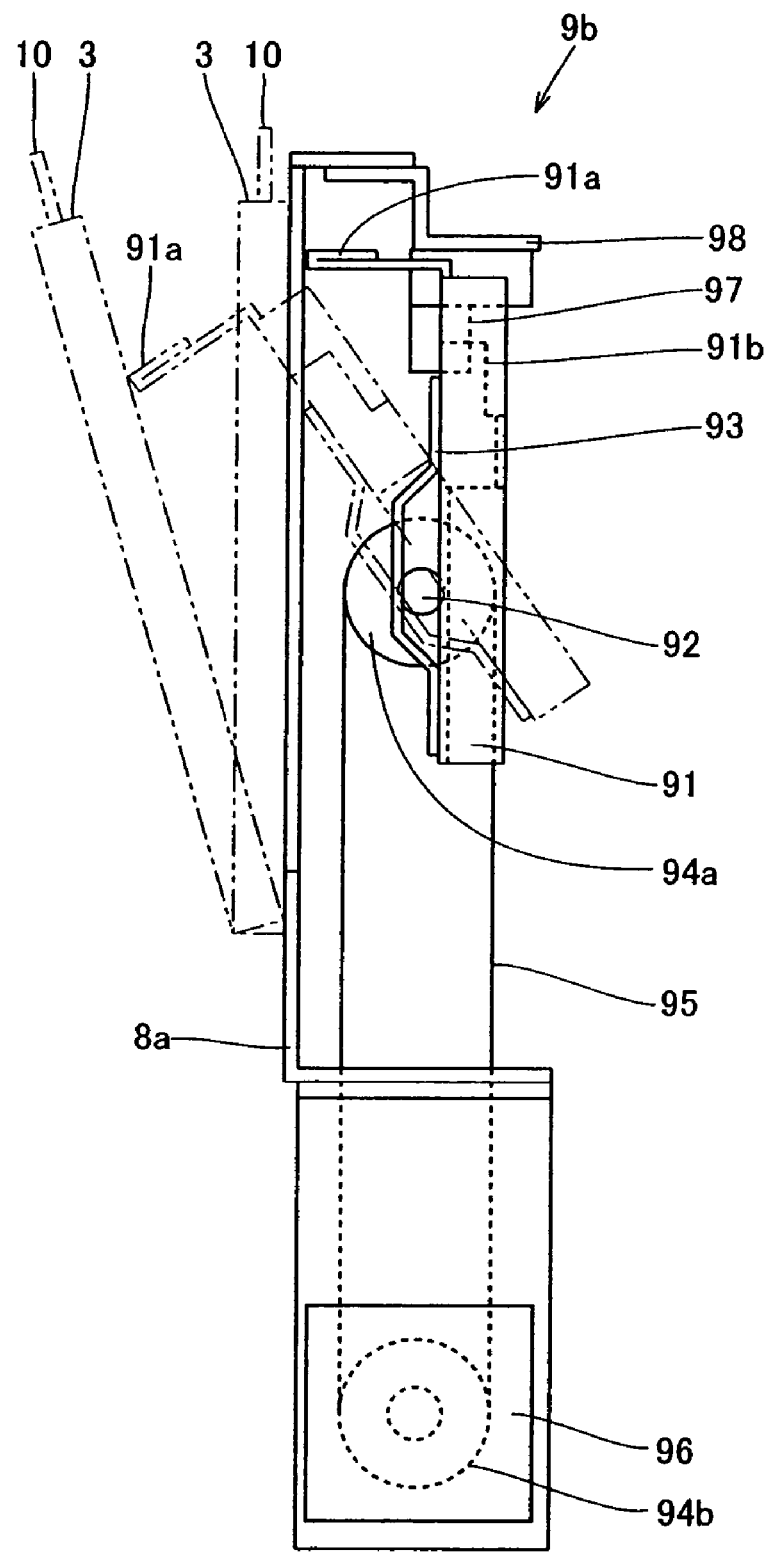
FIG. 17 is a side elevational view for illustrating operations of the feed part of the keeping part shown in FIG. 16.

The structure of the feed part 9b of the keeping part 9 according to this embodiment is now described in detail with reference to FIGS. 3, 16 and 17. As shown in FIG. 16, the feed part 9b is constituted of a swinging member 91 of sheet metal, a support shaft 92 of metal, a mounting member 93 of sheet metal, pulleys 94a and 94b, a driving belt 95 and a drive motor 96. The swinging member 91 is provided for pressing the cassettes 3 and moving the same toward the keeping part 9 (see FIG. 3), as shown in FIG. 17. This swinging member 91 has a swinging section 91a, which swings to press upper portions of the cassettes 3. The swinging member 91 is also integrally provided with a detector 91b for detecting presence of the swinging member 91 on a stationary position (non-swinging position), as shown in FIG. 16. A light transmission sensor 97 for sensing the detector 91b of the swinging member 91 is mounted on the frame 8a through a bracket 98. As shown in FIGS. 16 and 17, the mounting member 93 presses the support shaft 92 against the swinging member 91. Thus, the support shaft 92 is fixed to the swinging member 91. The pulleys 94a and 94b are connected to an end of the support shaft 92 and the drive motor 96 respectively. The driving belt 95 is mounted on the pulleys 94a and 94b. The transport part 9 is provided with the transport belt 9c for transporting the cassettes 3 moved toward the keeping part 9 by the feed part 9c, as shown in FIG. 3.

According to this embodiment, the control part 110 of the blood smear preparation apparatus 100 has a function of controlling whether to transport the cassettes 3 storing the stained slide glasses 10 to the port 9a of the keeping part 9 or to the inlet 300a of the automatic blood cell analyzer 300. The control part 110 further controls operations of the second cassette transport part 8 and the feed part 9b of the keeping part 9. This control part 110 is provided with a memory 111 storing specimen information such as specimen preparation conditions.

As shown in FIG. 3, the automatic blood cell analyzer 300 comprises a feed part 301, a cassette storage part 302, a slide glass unloading part 303, a bar code reading part 304, an analysis part 305 and a control part 306. The feed part 301, having a structure similar to that of the feed part 9b of the keeping part 9 in the blood smear preparation apparatus 100 shown in FIG. 16, is set on a region corresponding to the inlet 300a of the automatic blood cell analyzer 300. The feed part 301 is provided for moving the cassettes 3 transported to the inlet 300a of the automatic blood cell analyzer 300 toward the cassette storage part 302. The cassette storage part 302 has a structure similar to that of the keeping part 9 in the blood smear preparation apparatus 100. This cassette storage part 302 is provided with a pair of transport belts 302a. The slide glass unloading part 303 has a function of unloading the stained slide glasses 10 from the cassettes 3 and transporting the same to the bar code reading part 304. The bar code reading part 304 has a function of reading the two-dimensional bar code 10b (see FIG. 4) printed on the frosted part 10a of each slide glass 10. The analysis part 305 has a function of digitally image-processing the specimens of the stained slide glasses 10 while automatically classifying blood cells.

Operations of the specimen preparation/analysis system according to this embodiment are now described with reference to FIGS. 1 to 18.

As a sucking/dispensing operation, an operator presses the starting switch 102 to start the blood smear preparation apparatus 100, for setting the sample rack 150 storing the test tubes 151 storing blood samples on a receiving part 201 of the transporter 200, as shown in FIG. 1. Then, the operator presses a start switch for automatic suction displayed on the display operation part 101, for transporting the sample rack 150 to an unloading part 202 of the transporter 200. Thereafter the hand member 160 of the blood smear preparation apparatus 100 grasps one of the test tubes 151 storing blood from the sample rack 150. The hand member 160 moves up and rotates to lift up the test tube 151 and stir the contents thereof, and thereafter arranges the test tube 151 on the sucking/dispensing mechanism part 1 shown in FIG. 3. The sucking/dispensing mechanism part 1 inserts the piercer 1a into the rubber stopper 151a of the test tube 151 for sucking the blood. In this suction, the valves 1d and 1e are opened (on) and blocked (off) respectively. After completion of this suction, the valves 1d and 1e are blocked (off) and opened (on) respectively. Thereafter the pipette 1b is moved to the dispensing/smearing position 20 shown in FIG. 3.

In parallel with the sucking/dispensing operation, the cassettes are introduced with the cassette storage part 4 shown in FIG. 3. More specifically, the cassettes 3 are first set on the cassette storage part 4. Thus, the feeding belt 4a of the cassette storage part 4 engages with the transport belt engaging parts 3g (see FIGS. 5 and 6) of the cassettes 3, for feeding the same into a cassette standby position 40. The first one of the cassettes 3 fed into the cassette standby position 40 is arranged on the transport path 5c.

Figure 2:
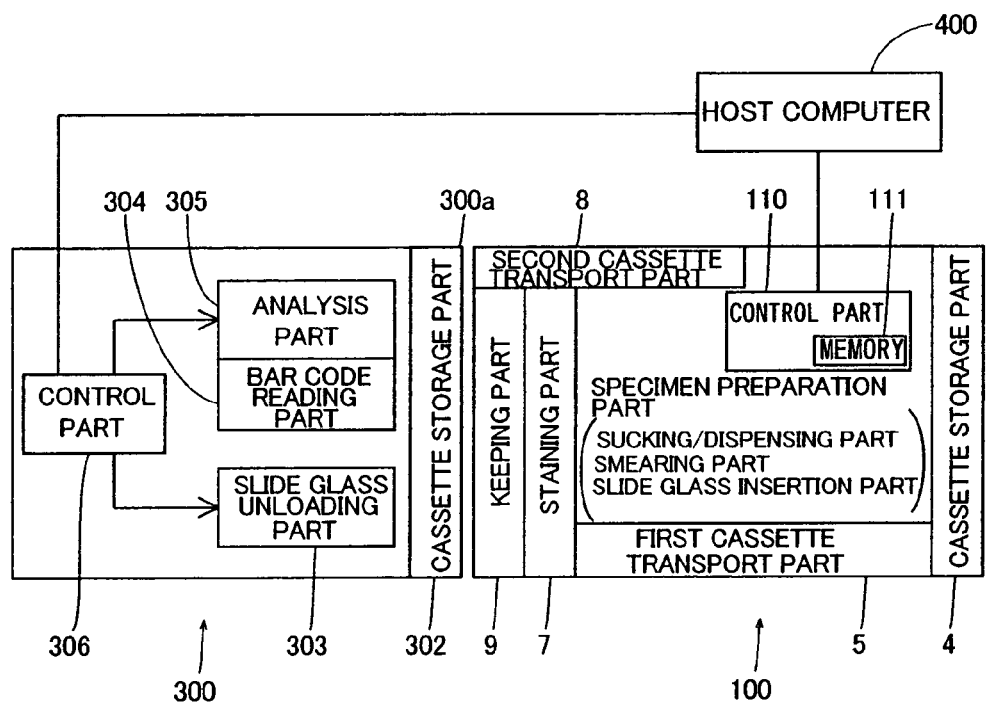
FIG. 2 is a schematic diagram of the specimen preparation/analysis system according to the embodiment shown in FIG. 1.
Figure 18:
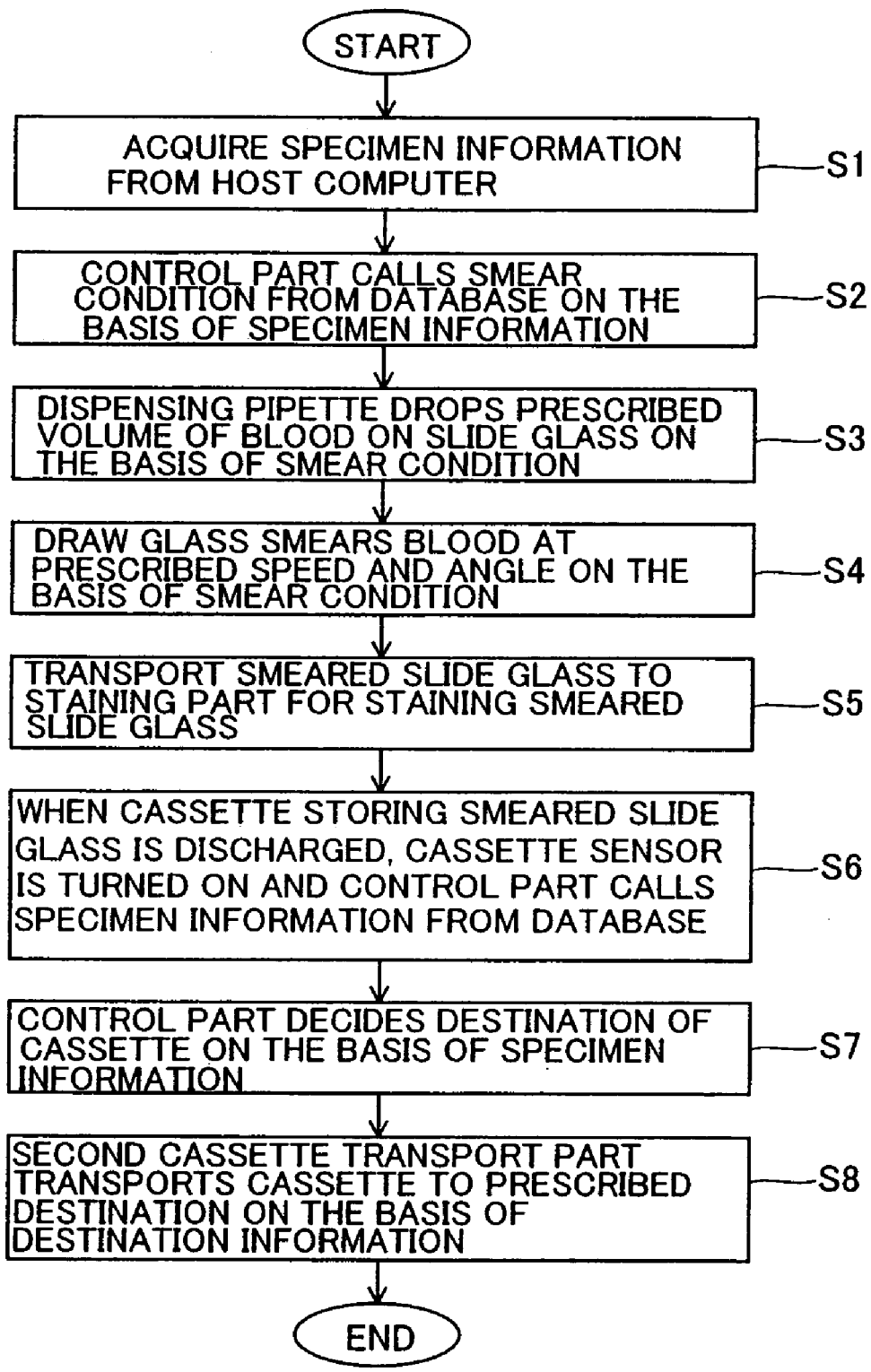
FIG. 18 is a flow chart for illustrating operations of the specimen preparation/analysis system according to the embodiment of the present invention.

At a step S1 of a flow chart shown in FIG. 18, the control part 110 of the blood smear preparation apparatus 100 acquires specimen information from the host computer 400 (see FIG. 2). This specimen information includes information such as sample numbers and the number of prepared smears etc. The specimen information also includes information as to whether to prepare either or both of visually recognized and automatically analyzed specimens etc. The specimen information further includes information as to whether or not to analyze the specimens in the automatic blood cell analyzer 300. At a step S2, the control part 110 calls smear conditions from a database stored therein. In the smear conditions for preparing smears, the volume of dropped blood, the angle of the draw glass 2c, the traveling speed of the draw glass 2c etc. have been previously set in correspondence to desired smears. At a step S3, the blood is dropped on (dispensed to) each slide glass 10 with the pipette 1b. In order to prepare both of automatically analyzed and visually recognized specimens, the sucking/dispensing apparatus 1 dispenses the same blood to two slide glasses 10 with the pipette 1b. In this case, the sucking/dispensing apparatus 1 dispenses the blood in a volume corresponding to the automatically analyzed specimen for preparing the automatically analyzed specimen, while dispensing the blood in a volume corresponding to the visually recognized specimen for preparing the visually recognized specimen.

At a step S4, the smearing part 2 smears the blood on the basis of the smear conditions in parallel with or after the aforementioned sucking/dispensing operation by the sucking/dispensing mechanism part 1. As shown in FIG. 3, the smearing part 2 supplies the slide glasses 10 to the dispensing/smearing position 20, for smearing the blood dropped on the slide glasses 10, drying the same and printing information on the slide glasses 10. More specifically, the unloading mechanism (not shown) and the feeding belts 2e supply the slide glasses 10 stored in the two slide glass storage parts 2b of the slide glass supply part 2a onto the feeding belts 2e. Then, the feeding belts 2e transport the slide glasses 10 to the dispensing/smearing position 20. The slide glasses 10 have been transported to the dispensing/smearing position 20 before the aforementioned sucking/dispensing operation. In this state, the sucking/dispensing mechanism part 1 drops (dispenses) the blood on (to) the slide glasses 10 with the pipette 1b.

Thereafter the draw glass 2c moves to come into contact with the slide glasses 10 and reciprocates longitudinally along the slide glasses 10, thereby smearing the slide glasses 10 with the blood dropped thereon on the dispensing/smearing position 20. At this time, the contact angle of the draw glass 2c with respect to the slide glasses 10 and the speed of reciprocation thereof are varied with the automatically analyzed and visually recognized specimens. More specifically, the angle and the speed are so regulated that the automatically analyzed specimens are smaller in thickness than the visually recognized specimens. Thereafter the feeding belts 2e transport the smeared slide glasses 10 to the drying positions 21a. Then, the fan 2f dries the blood smeared on the slide glasses 10 with cold air on the two adjacent drying position 21a and 21b twice. Thereafter the slide glass transport part 2h moves the smeared slide glasses 10 to the printing part 2g. The smearing part 2 prints the two-dimensional bar code 10b storing the specimen information such as the sample number, the date, the serial number and the name and the three rows of texts 10c formed by Chinese characters of the date and the name etc. on the frosted part 10a of each slide glass 10 on the printing part 2g.

Then, the cassette transport part 5 transports the cassettes 3 arranged on the transport path 5c one by one to the slide glass insertion part 6. In other words, the cassette transport member 5a constituting the cassette transport part 5 moves from the transport starting position 50 while pressing the side face parts 3h (see FIGS. 5 and 6) of the cassettes 3, thereby transporting the cassettes 3 to the slide glass insertion part 6.

At a step S5, the cassette transport part 5 stores the smeared slide glasses 10 in the cassettes 3 and transports the same to the staining part 7 with the cassette transport member 5a for staining the slide glasses 10.

More specifically, the cassette rotation mechanism part 6a rotates in a prescribed direction for moving the cassettes 3 from a vertical position to a horizontal position shown by two-dot chain lines in FIG. 3, to be capable of receiving the slide glasses 10. In this state, the vertical mover 2j of the smearing part 2 advances for inserting the smeared slide glasses 10 into the slide glass receiving holes 3a of the cassettes 3. Thus, the cassettes 3 store the smeared slide glasses 10. Thereafter the cassette rotation mechanism part 6a rotates oppositely to the aforementioned prescribed direction, thereby returning the cassettes 3 to the original vertical position. In the staining part 7, the first sucking/discharging part 7c lifts up the smeared slide glasses 10 from the slide glass storage holes 3a of the cassettes 3 for dispensing methanol to the stain sucking/dispensing holes 3b of the cassettes 3. Then the staining part 7 returns the smeared slide glasses 10 to the cassettes 3, so that the feed member 7a places the cassettes 3 storing the smeared slide glasses 10 one by one on the transport belts 7b. The transport belts 7b transport the cassettes 3 to the second sucking/discharging part 7d.

The second sucking/discharging part 7d lifts up the smeared slide glasses 10 from the slide glass receiving holes 3a of the cassettes 3 and dries the same by applying a blast from the fan 7j to the smeared faces of the slide glasses 10 for about 1 second to about 60 seconds, thereby evaporating the liquid component on the smeared faces and drying the smeared faces. The time (dipping time) for dipping the smeared slide glasses 10 in methanol with the first sucking/discharging part 7c and lifting up the same with the second sucking/discharging part 7d is about 20 seconds to about 120 seconds.

Then, the staining part 7 performs staining (May-Grünwald/Giemsa double staining). First, the second sucking/discharging part 7d sucks methanol from the stain sucking/dispensing holes 3b of the cassettes 3, discharges the same, and thereafter returns the slide glasses 10 to the slide glass receiving holes 3a of the cassettes 3. Then, the staining part 7 dispenses May-Grünwald stain (mainly composed of 99% of methanol) through the stain sucking/dispensing holes 3b of the cassettes 3 and dips the smeared slide glasses 10 in the May-Grünwald stain. Thus, the staining part 7 starts May-Grünwald/Giemsa double staining. The staining part 7 dips the smeared slide glasses 10 in the May-Grünwald stain for about 1 minute to about 5 minutes while transporting the cassettes 3 with the transport belts 7b. The third sucking/discharging part 7e sucks the May-Grünwald stain from the stain sucking/dispensing holes 3b of the cassettes 3, discharges the same, and thereafter dispenses diluted May-Grünwald stain to the stain sucking/dispensing holes 3b of the cassettes 3. The staining part 7 dips the smeared slide glasses 10 in the diluted May-Grünwald stain for about 1 minute to about 5 minutes while transporting the cassettes 3 with the transport belts 7b. The fourth sucking/discharging part 7f sucks the diluted May-Grünwald stain from the stain sucking/dispensing holes 3b of the cassettes 3, discharges the same, and thereafter dispenses diluted Giemsa stain to the stain sucking/dispensing holes 3b of the cassettes 3. The staining part 7 dips the smeared slide glasses 10 in the diluted Giemsa stain for about 1 minute to about 20 minutes while transporting the cassettes 3 with the transport belts 7b.

Then, the fifth sucking/discharging part 7g sucks the diluted Giemsa stain from the stain sucking/dispensing holes 3b of the cassettes 3, discharges the same, and thereafter dispenses and sucks a cleaning fluid to and from the stain sucking/dispensing holes 3b of the cassettes 3 for washing the smeared slide glasses 10. Thereafter the staining part 7 dries the stained slide glasses 10 with the fan 7h.

At a step S6, the control part 110 turns on the cassette sensor 87 of the cassette detection part 8c of the second cassette transport part 8, thereby calling the specimen information from the database stored in the control part 110. More specifically, the cassettes 3 storing the stained slide glasses 10 are transported from the smearing part 7 to the transport starting position 80 of the second cassette transport part 8. At this time, each cassette 3 presses the bent part 88a of the detector 88 of the cassette detection part 8c outward beyond the frame 8a, as shown in FIG. 13. Thus, the detection part 88b of the detector 88 moves outward beyond the frame 8a, thereby turning on the cassette sensor 87. Consequently, the control part 110 calls the specimen information from the database stored in the memory 111 thereof.

At a step S7, the control part 110 decides the destination of the cassettes 3 storing the stained slide glasses 10 on the basis of the specimen information. In other words, the control part 110 decides whether to transport the cassettes 3 to the port 9a of the keeping part 9 of the blood smear preparation apparatus 100 or to the inlet 300a of the automatic blood cell analyzer 300.

At a step S8, the second transport part 8 transports the cassettes 3 storing the stained slide glasses 10 to the decided destination on the basis of information on the destination decided in the control part 110. More specifically, the drive motor 86 drives the driving belt 84 thereby moving the moving member 81 coupled to the driving belt 84 along arrow C, as shown in FIG. 10. Thus, the contact parts 81a and 81b of the moving member 81 come into contact with the side face parts 3h and 3j of the cassettes 3 respectively. Consequently, the contact parts 81a and 81b of the moving member 81 press and move the cassettes 3 along arrow C. At this time, the cassettes 3 move along the transport paths 8d and 8e arranged on the prescribed region in the blood smear preparation apparatus 100 and at the inlet 300a of the automatic blood cell analyzer 300 respectively.

Figure 14:
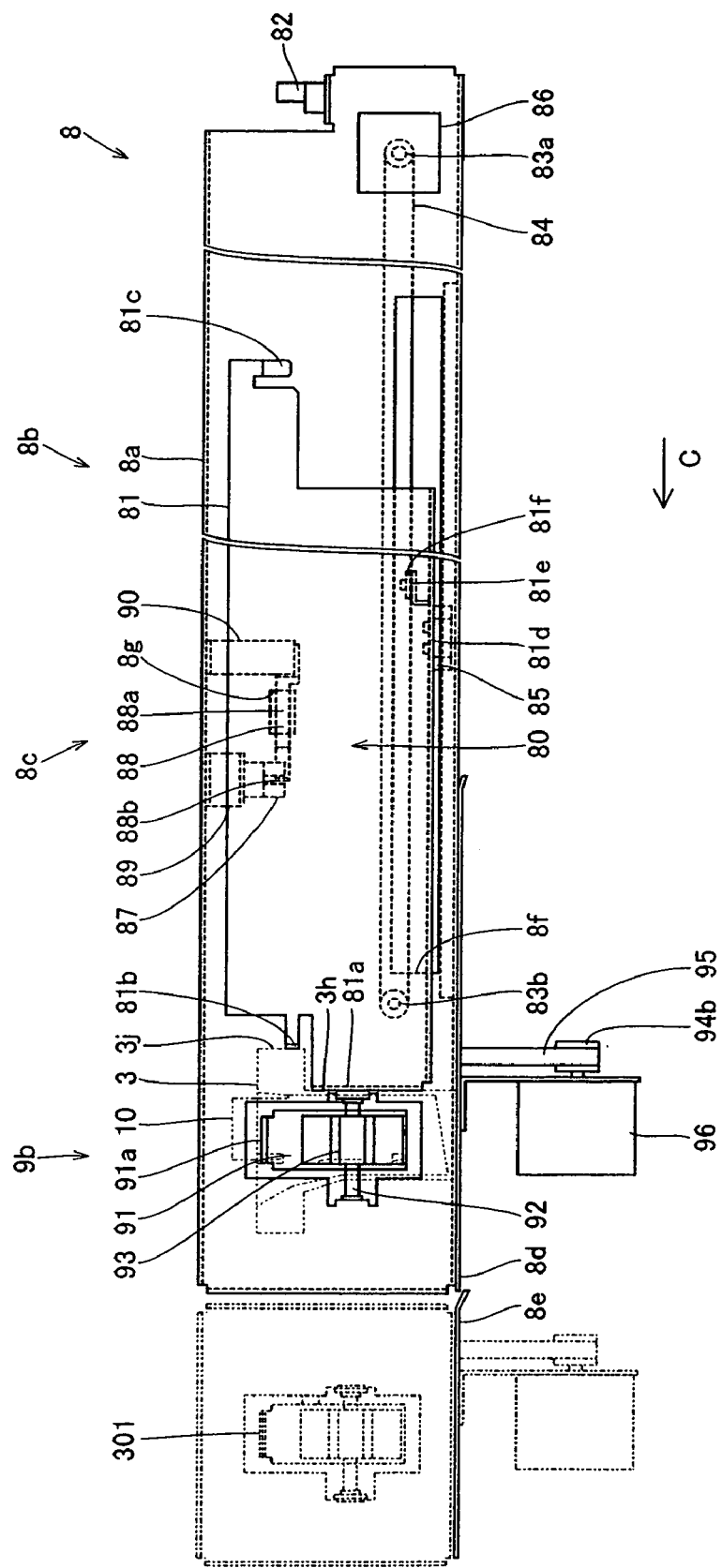
FIGS. 14 and 15 are plan views for illustrating operations of the second cassette transport part of the specimen preparation apparatus of the specimen preparation/analysis system according to the embodiment shown in FIG. 1.
Figure 15:
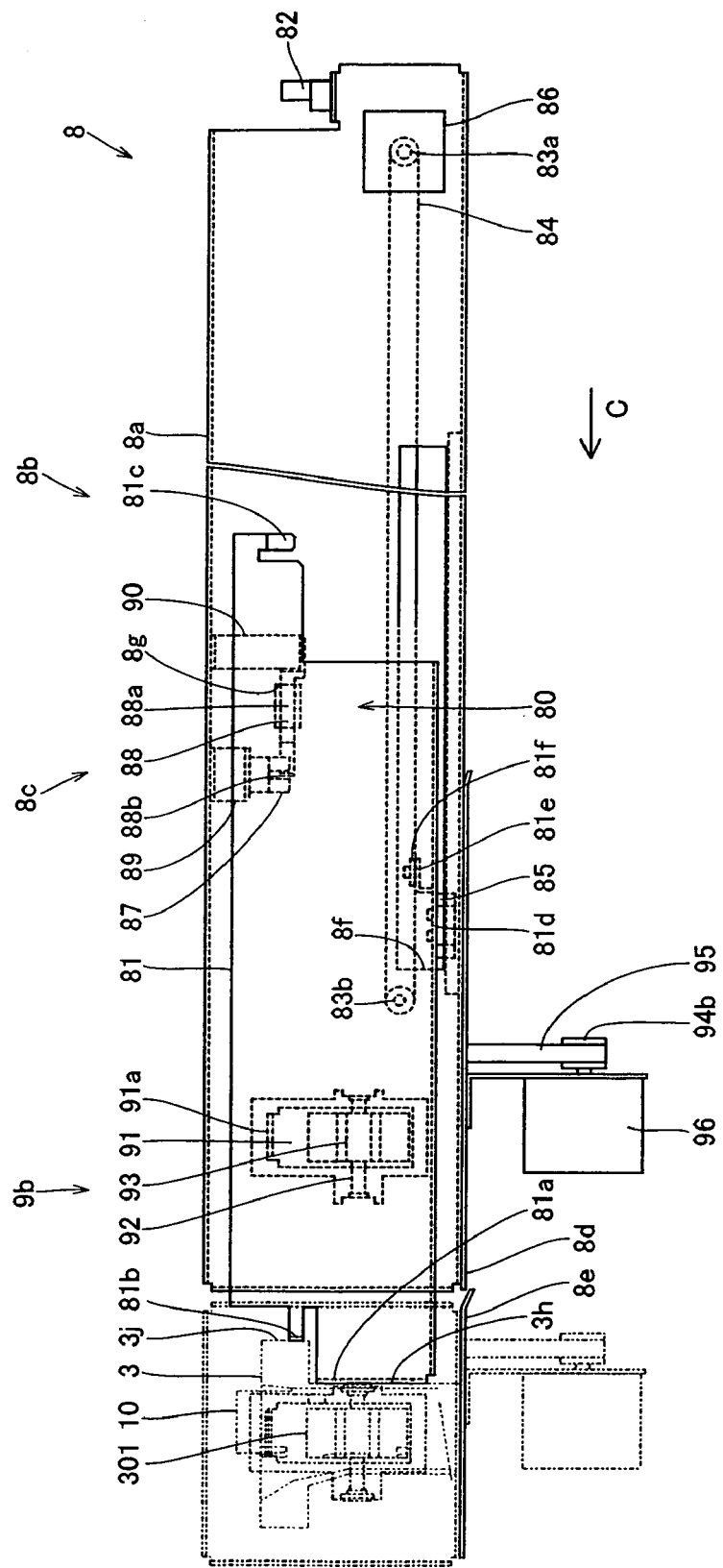

According to this embodiment, the control part 110 controls the pulse number of the drive motor 86 on the basis of the decided destination information. More specifically, the control part 110 controls the movement of the moving member 81 along arrow C for completing movement of the cassettes 3 along arrow C on the port 9a as shown in FIG. 14, in order to transport the cassettes 3 storing the stained slide glasses 10 to the port 9a (see FIG. 3) of the keeping part 9 of the blood smear preparation apparatus 100. In order to transport the cassettes 3 storing the stained slide glasses 10 to the inlet 300a (see FIG. 3) of the automatic blood cell analyzer 300, on the other hand, the control part 110 controls the movement of the moving member 81 along arrow C for completing movement of the cassettes 3 along arrow C on the inlet 300a, as shown in FIG. 15. The second cassette transport part 8 transports the cassettes 3 in this manner, thereby terminating the operation flow shown in FIG. 18.

Then, the feed part 9b of the keeping part 9 moves the cassettes 3 storing the stained slide glasses 10 transported to the port 9a of the keeping part 9 of the blood smear preparation apparatus 100 toward the keeping part 9, as shown in FIG. 3. More specifically, the drive motor 96 rotates to drive the driving belt 95, thereby rotating the swinging member 91 in the same direction as the drive motor 96 as shown in FIG. 17. Thus, the swinging section 91a of the swinging member 91 presses upper portions of the cassettes 3, thereby moving the cassettes 3 toward the keeping part 9 (see FIG. 3). The control part 110 controls this operation of the feed part 9b. Thereafter the transport belt 9c transports the cassettes 3 to the keeping part 9, which in turn keeps the cassettes 3, as shown in FIG. 3.

On the other hand, the feed part 301 presses the cassettes 3 storing the stained slide glasses 10 transported to the inlet 300a of the automatic blood cell analyzer 300 toward the cassette storage part 302, while the transport belts 302a transport the cassettes 3 to the cassette storage part 302. At this time, the feed part 301 of the automatic blood cell analyzer 300 operates similarly to the feed part 9b of the keeping part 9. Thereafter the slide glass unloading part 303 unloads the stained slide glasses 10 from the cassettes 3 and transports the same to the bar code reading part 304. Then, the bar code reading part 304 reads the two-dimensional bar codes 10b printed on the frosted parts 10a of the slide glasses 10. The bar code reading part 304 transmits the read sample numbers of the stained slide glasses 10 to the control part 306, which in turn inquires the sample numbers from the host computer 400. Thus, the control part 306 confirms whether or not the stained slide glasses (specimens) 10 must be analyzed before transporting the same to the analysis part 305. If the stained slide glasses (specimens) 10 must be analyzed, the analysis part 305 digitally image-processes the stained slide glasses (specimens) 10 while automatically classifying blood cells. Thereafter the stained slide glasses (specimens) 10 subjected to blood cell classification are stored in a magazine (not shown) for analyzed specimens. When no analysis is necessary, on the other hand, the stained slide glasses (specimens) 10 are not analyzed in the analysis part 305 but stored in the magazine (not shown) for analyzed specimens. The control part 306 controls the operations of the slide glass unloading part 303 and the analysis part 305.

According to this embodiment, as hereinabove described, the blood smear preparation apparatus 100 is provided with the second cassette transport part 8 for transporting the cassettes 3 storing the stained slide glasses (specimens) 10 to the inlet 300a of the automatic blood cell analyzer 300 so that the second cassette transport part 8 can automatically supply specimens from the blood smear preparation apparatus 100 to the automatic blood cell analyzer 300. Thus, the specimen preparation/analysis system can supply the specimens from the blood smear preparation apparatus 100 to the automatic blood cell analyzer 300 without burdening the operator.

According to this embodiment, the second cassette transport part 8 also has the function of transporting the cassettes 3 storing the stained slide glasses 10 to the port 9a of the keeping part 9 of the blood smear preparation apparatus 100, whereby the single second cassette transport part 8 can distribute the cassettes 3 storing the stained slide glasses 10 to the port 9a of the keeping part 9 and the inlet 300a of the automatic blood cell analyzer 300 when the blood smear preparation apparatus 100 prepares two types of specimens, i.e., those supplied to the automatic blood cell analyzer 300 and those kept in the keeping part 9.

According to this embodiment, the blood smear preparation apparatus 100, provided with the control part 110 controlling the second cassette transport 8 to transport the cassettes 3 storing the stained slide glasses 10 to the port 9a of the keeping part 9 or the inlet 300a of the automatic blood cell analyzer 300, can easily distribute the cassettes 3 storing the stained slide glasses 10 to the port 9*a* of the keeping part 9 and the inlet 300*a* of the automatic blood cell analyzer 300 respectively.

According to this embodiment, the keeping part 9 of the blood smear preparation apparatus 100 is provided with the feed part 9*b* moving the cassettes 3 transported to the port 9*a* of the keeping part 9 toward the keeping part 9 while the control part 110 controls the feed part 9*b* to move the cassettes 3 toward the keeping part 9 when the second cassette transport part 8 transports the stained slide glasses 10 to the port 9*a* of the keeping part 9, whereby the second transport part 8 can easily move the cassettes 3 storing the stained slide glasses 10 transported to the port 9*a* of the keeping part 9 toward the keeping part 9.

According to this embodiment, the second cassette transport part 8, provided with the moving member 81 coming into contact with the cassettes 3 for moving the same and the drive motor 86 driving the moving member 81, can easily transport the cassettes 3 to the inlet 300*a* of the automatic blood cell analyzer 300 with the moving member 81.

According to this embodiment, the moving member 81 of the second cassette transport part 8 is provided with the contact parts 81*a* and 81*b* coming into contact with the side face parts 3*h* and 3*j* of the cassettes 3 respectively so that the contact parts 81*a* and 81*b* of the moving member 81 can come into contact with the side face parts 3*h* and 3*j* of the cassettes 3 respectively, whereby the second cassette transport part 8 can stably transport the cassettes 3 to the inlet 300*a* of the automatic blood cell analyzer 300.

According to this embodiment, the second cassette transport part 8 is provided with the transport paths 8*d* and 8*e* arranged on the prescribed region in the blood smear preparation apparatus 100 and at the inlet 300*a* of the automatic blood cell analyzer 300 respectively to be capable of moving the cassettes 3 from the transport starting position 80 to the inlet 300*a* of the automatic blood cell analyzer 300 through the port 9*a* of the keeping part 9 of the blood smear preparation apparatus 100 along the transport paths 8*d* and 8*e*, whereby the second transport part 8 can easily transport the cassettes 3 to the port 9*a* of the keeping part 9 of the blood smear preparation apparatus 100 or the inlet 300*a* of the automatic blood cell analyzer 300.

According to this embodiment, the cassette detection part 8*c*, provided on the transport starting position 80 of the second cassette transport part 8 for detecting arrival of the cassettes 3 storing the stained slide glasses 10, can easily detect arrival of the cassettes 3 storing the stained slide glasses 10 on the transport starting position 80 of the second cassette transport part 8.

According to this embodiment, the sucking/dispensing mechanism part 1 has the function of dispensing the same blood (specimen) on two slide glasses 10 while regulating the volume of the dispensed blood to those corresponding to the automatically analyzed and visually observed specimens respectively, whereby the specimen preparation/analysis system can easily prepare the specimen analyzed in the automatic blood cell analyzer 300 and the visually recognized specimen from the same blood.

According to this embodiment, the blood smear preparation apparatus 100 is provided with the printing part 2*g* for printing the two-dimensional bar codes 10*b* storing the specimen information on the frosted parts 10*a* of the slide glasses 10 while the automatic blood cell analyzer 300 is provided with the bar code reading part 304 reading the two-dimensional bar codes 10*b*, whereby the contents of the specimen information printed on the frosted parts 10*a* of the slide glasses 10 can be increased through the two-dimensional bar codes 10*b* capable of storing larger quantities of information than one-dimensional bar codes. Also when the second cassette transport part 8 automatically supplies the cassettes 3 storing the stained slide glasses (specimens) 10 to the automatic blood cell analyzer 300, confusion between the specimens can be suppressed by confirming the specimen information through the bar code reading part 304 before the automatic blood cell analyzer 300 analyzes the specimens.

According to this embodiment, the two-dimensional bar code 10*b* storing the specimen information is printed on the frosted part 10*a* of each slide glass 10 so that the slide glass 10 can hold a large quantity of detailed specimen information due to the two-dimensional bar code 10*b* capable of storing a larger quantity of information than a one-dimensional bar code. Consequently, the operator can confirm a large quantity of detailed specimen information related to a prescribed slide glass (specimen) 10 by reading the two-dimensional bar code 10*b* printed on the prescribed slide glass 10 without inquiring the corresponding specimen information from the host computer 400. In this case, the text data (10*c* to 10*e*) are also printed on the frosted part 10*a* of the slide glass 10 as the specimen information in addition to the two-dimensional bar code 10*b* so that the size of the print area of the two-dimensional bar code 10*b* can be reduced through the large quantity of information storable in the two-dimensional bar code 10*b*, whereby the size of the print area of the text data (10*c* to 10*e*) can be increased. Thus, the slide glass 10 can hold a large quantity of text data (10*c* to 10*e*) as the specimen information. Therefore, when the two-dimensional bar code 10*b* printed on the prescribed slide glass 10 is hard to read, for example, the operator can confirm the large quantity of specimen information related to the prescribed slide glass (specimen) 10 through the visually recognizable text data (10*c* to 10*e*) without inquiring the specimen information of the corresponding slide glass 10 from the host computer 400.

According to this embodiment, the bar code print area F1 and the text print area F2 of the frosted part 10*a* printed with the two-dimensional bar code 10*b* and the text data (10*c* to 10*e*) respectively are arranged to be adjacent to each other along the shorter direction of the slide glass 10 so that the length of the specimen preparation area 10*f* along the longitudinal direction of the slide glass 10 can be increased as compared with a case of arranging the bar code print area F1 and the text print area F2 to be adjacent to each other along the longitudinal direction of the slide glass 10 having the frosted part 10*a* arranged on the region closer to one end of the slide glass 10 along the longitudinal direction thereof. Thus, the size of the specimen preparation area 10*f* of the slide glass 10 having the frosted part 10*a* arranged on the region closer to one end of the slide glass 10 along the longitudinal direction thereof is not reduced despite the bar code print area F1 and the text print area F2 arranged on the frosted part 10*a*. In this case, the two-dimensional bar code 10*b* is so formed in the square shape in plan view that the text print area F2 remains unchanged also when the direction of arrangement of the two-dimensional bar code 10*b* is changed.

According to this embodiment, the text data (10*c* to 10*e*), divided into the three rows of different types of data, i.e., the date 10*c*, the name 10*d* and the sample number 10*c*, are easier to read as compared with a case of wholly displaying the date 10*c*, the name 10*d* and the sample number 10*c* in one row. In this case, the three rows of text data (10*c* to 10*e*) are arranged to be adjacent to each other along the longitudinal direction of the slide glass 10 while the characters and numerals constituting the text data (10*c* to 10*e*) respectively are arranged along the shorter direction of the slide glass 10, whereby the text data (10*c* to 10*e*) are more easily readable.

According to this embodiment, the three rows of text data (10c to 10e) are so arranged that the lengths of the bar code print area F1 and the text print area F2 are equal to each other along the longitudinal direction of the slide glass 10, whereby the frosted part 10a of the slide glass 10 can be inhibited from wasting of a dead region provided with no specimen information.

According to this embodiment, the printable coating film 10g is formed on the region of the slide glass 10 corresponding to the frost part 10a while the two-dimensional bar code 10b and the three rows of text data (10c to 10e) are printed on the upper surface of the coating film 10g located on the frosted part 10a, whereby the frosted part 10a of the slide glass 10 can easily display the specimen information (the sample number, the date, the serial number and the name). In this case, the coating film 10g is formed to extend from the frosted part 10a along the longitudinal direction of the slide glass 10 for holding the specimen preparation area 10f, so that a plurality of slide glasses 10 superposed with each other can be inhibited from adhering to each other.

Although the present invention has been described and illustrated in detail, it is clearly understood that the same is by way of illustration and example only and is not to be taken by way of limitation, the spirit and scope of the present invention being limited only by the terms of the appended claims.

For example, while the present invention is applied to the specimen preparation/analysis system comprising the blood smear preparation apparatus in the aforementioned embodiment, the present invention is not restricted to this but is also applicable to a specimen preparation/analysis system comprising a specimen preparation apparatus other than the blood smear preparation apparatus.

While the present invention is applied to the specimen preparation/analysis system comprising the automatic blood cell analyzer in the aforementioned embodiment, the present invention is not restricted to this but is also applicable to a specimen preparation/analysis system comprising a specimen analyzer other than the automatic blood cell analyzer.

While the blood smear preparation apparatus is provided with the keeping part and the specimens prepared in the blood smear preparation apparatus are distributed to the port of the keeping part and the inlet of the automatic blood cell analyzer in the aforementioned embodiment, the present invention is not restricted to this but all specimens prepared in the blood smear preparation apparatus may alternatively be transported to the inlet of the automatic blood cell analyzer with no keeping part provided on the blood smear preparation apparatus.

While the moving member having the contact parts coming into contact with the side face parts of the cassettes storing the stained slide glasses transports the cassettes in the aforementioned embodiment, the present invention is not restricted to this but a further driving belt may engage with the cassettes for transporting the cassettes.

While the second transport part transports the cassettes storing the stained slide glasses to the inlet of the automatic blood cell analyzer in the aforementioned embodiment, the present invention is not restricted to this but the second transport part may alternatively unload the stained slide glasses from the cassettes for transporting only the stained slide glasses to the inlet of the automatic blood cell analyzer. In this case, the specimen preparation/analysis system including the blood smear preparation apparatus and the automatic blood cell analyzer preferably has a structure such as that of a first modification of the embodiment shown in FIG. 19.

Figure 19:
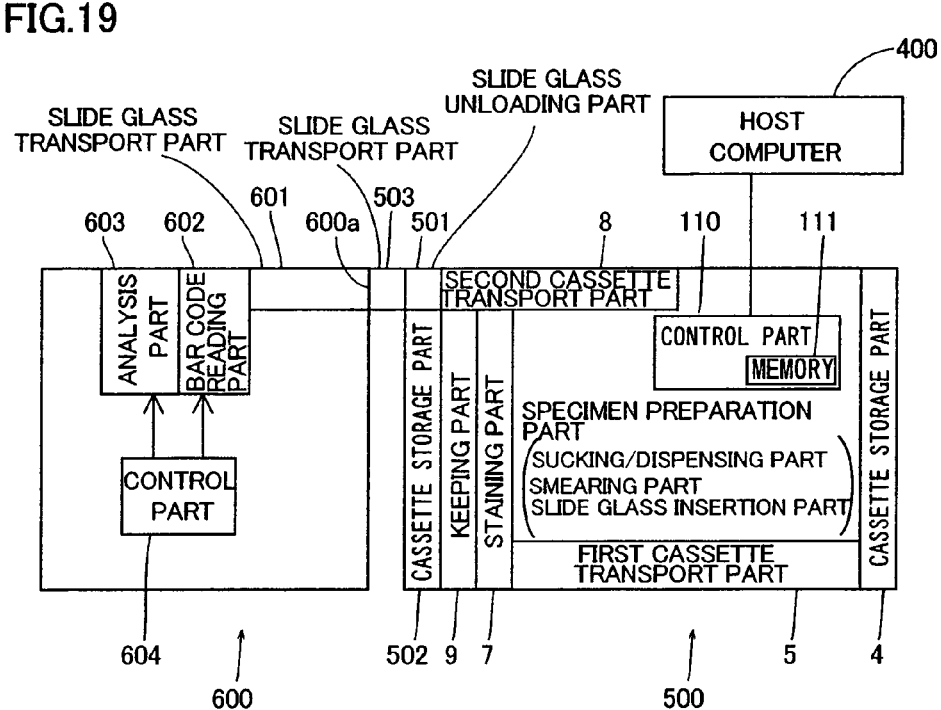
FIG. 19 is a schematic diagram showing a specimen preparation/analysis system according to a first modification of the embodiment.

More specifically, a specimen preparation/analysis system according to the first modification of the embodiment shown in FIG. 19 comprises a blood smear preparation apparatus 500 and an automatic blood cell analyzer 600. The blood smear preparation apparatus 500 according to the first modification includes a sucking/dispensing mechanism part, a smearing part, resin cassettes (not shown), a cassette storage part 4, a first cassette transport part 5, a slide glass insertion part, a staining part 7, a second cassette transport part 8, a keeping part 9 and a control part 110 similar to those of the aforementioned embodiment. The control part 110 is connected to a host computer 400.

The blood smear preparation apparatus 500 of the specimen preparation/analysis system according to the first modification further includes a slide glass unloading part 501, a cassette storage part 502 and a slide glass transport part 503. The slide glass unloading part 501 is provided for unloading stained slide glasses (not shown) from the cassettes transported by the second cassette transport part 8 from the staining part 7. This slide glass unloading part 501 has a chucking mechanism part (not shown) for holding and lifting up the slide glasses and placing the same on the slide glass transport part 503. The cassette storage part 502 is provided for storing the cassettes from which the stained slide glasses have been unloaded. The slide glass transport part 503 is provided for transporting the stained slide glasses unloaded from the cassettes by the slide glass unloading part 501 to an inlet 600a of the automatic blood cell analyzer 600. This slide glass transport part 503 has a pair of transport belts (not shown), similarly to each of the cassette storage part 4 and the keeping part 9.

The automatic blood cell analyzer 600 of the specimen preparation/analysis system according to the first modification of the embodiment includes a slide glass transport part 601, a bar code reading part 602, an analysis part 603 and a control part 604. The slide glass transport part 601 is provided for transporting the stained slide glasses transported to the inlet 600a by the slide glass transport part 503 of the blood smear preparation apparatus 500 to the bar code reading part 602. The bar code reading part 602 is provided for reading two-dimensional bar codes (not shown) printed on the slide glasses. The analysis part 603 is provided for digitally image-processing specimens of the stained slide glasses while automatically classifying blood cells. The control part 604 is provided for controlling operations of the bar code reading part 602 and the analysis part 603.

In the specimen preparation/analysis system according to the first modification of this embodiment, as hereinabove described, the blood smear preparation apparatus 500 is provided with the slide glass transport part 503 for transporting the stained slide glasses (specimens) unloaded from the cassettes to the inlet 600a of the automatic blood cell analyzer 600, whereby the slide glass transport part 503 can automatically supply the specimens (slide glasses) from the blood smear preparation apparatus 500 to the automatic blood cell analyzer 600. Thus, the specimen preparation/analysis system can supply the specimens (slide glasses) from the blood smear preparation apparatus 500 to the automatic blood cell analyzer 600 without burdening the operator.

In the specimen preparation/analysis system according to the first modification of this embodiment, the blood smear preparation apparatus 500 is provided with the slide glass unloading part 501 for unloading the stained slide glasses from the cassettes transported by the second cassette transport part 8 from the staining part 7, whereby the slide glass unloading part 501 can easily unload the stained slide glasses from the cassettes. Thus, the slide glass transport part 503 can easily transport the stained slide glasses unloaded from the cassettes to the inlet 600a of the automatic blood cell analyzer 600.

While the second cassette transport part transports the cassettes storing the stained slide glasses to the inlet of the automatic blood cell analyzer in the aforementioned embodiment, the present invention is not restricted to this but another unit may be provided for receiving the cassettes storing the stained slide glasses and supplying the same to the automatic blood cell analyzer so that the cassettes storing the stained slide glasses are transported to an inlet of this unit. In this case, the specimen preparation/analysis system including the blood smear preparation apparatus and the automatic blood cell analyzer preferably has a structure such as that of a second modification shown in FIG. 20.

Figure 20:
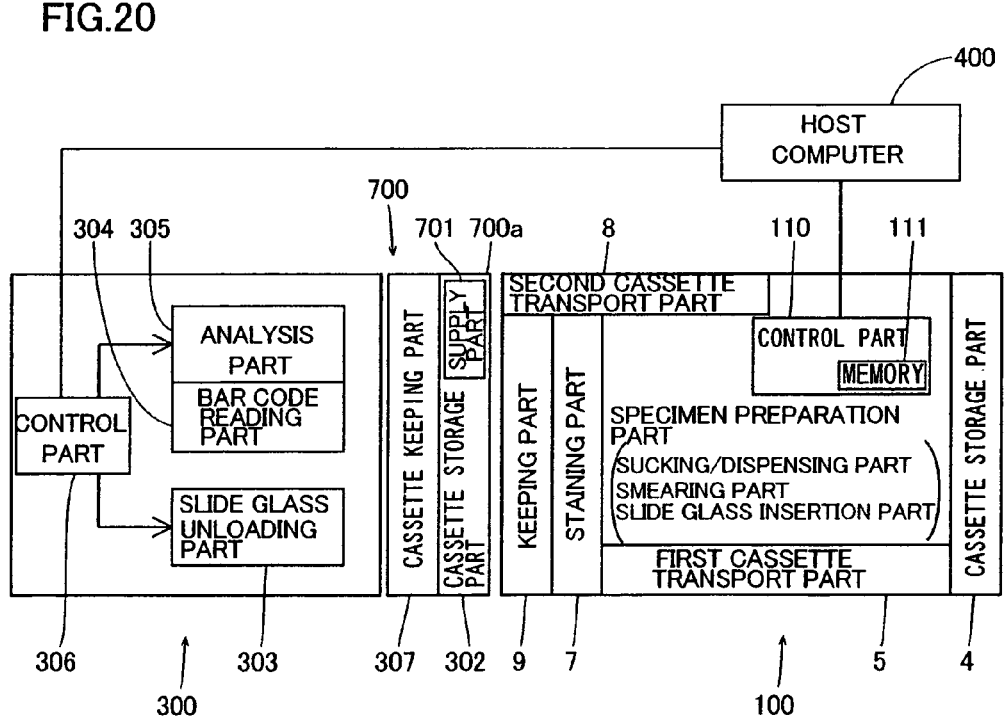
FIG. 20 is a schematic diagram showing a specimen preparation/analysis system according to a second modification of the embodiment.

More specifically, a specimen preparation/analysis system according to the second modification of the embodiment includes a cassette storage part 302 of an automatic blood cell analyzer 300 identical to that shown in FIG. 2 in a cassette supply unit 700 provided independently of the automatic blood cell analyzer 300, as shown in FIG. 20. The cassette storage part 302 of the cassette supply unit 700 is provided with a supply part 701 for supplying cassettes storing stained slide glasses to the automatic blood cell analyzer 300. The cassette storage part 302 of the cassette supply unit 700 stores the cassettes storing the stained slide glasses transported from the staining part 7 of the blood smear preparation apparatus 100 by the second cassette transport part 8 through the inlet 700a. The supply part 701 supplies the cassettes storing the stained slide glasses stored in the cassette storage part 302 of the cassette supply unit 700 to the automatic blood cell analyzer 300. The cassette supply unit 700 also includes a cassette keeping part 307. This cassette keeping unit 307 of the cassette supply unit 700 is provided for keeping the cassettes releasing the stained slide glasses after the slide glass unloading part 303 of the automatic blood cell analyzer 300 unloads the stained slide glasses from the cassettes. The remaining structure of the specimen preparation/analysis system according to the second modification of the embodiment is similar to that of the aforementioned embodiment.

As hereinabove described, the specimen preparation/analysis system according to the second modification of the embodiment, provided with the cassette supply unit 700 storing the cassettes storing the stained slide glasses and supplying the same to the automatic blood cell analyzer 300, can automatically supply the cassettes storing the stained slide glasses to the automatic blood cell analyzer 300 from the blood smear preparation apparatus 100 through the cassette supply unit 700. Thus, the specimen preparation/analysis system can automatically supply the cassettes storing the stained slide glasses to the automatic blood cell analyzer 300 from the blood smear preparation apparatus 100 without burdening the operator. Further, the specimen preparation/analysis system supplying the cassettes storing the stained slide glasses to the automatic blood cell analyzer 300 through the cassette supply unit 700 independent of the automatic blood cell analyzer 300 can easily solely operate the automatic blood cell analyzer 300 by removing the cassette supply unit 700.

Figure 21:
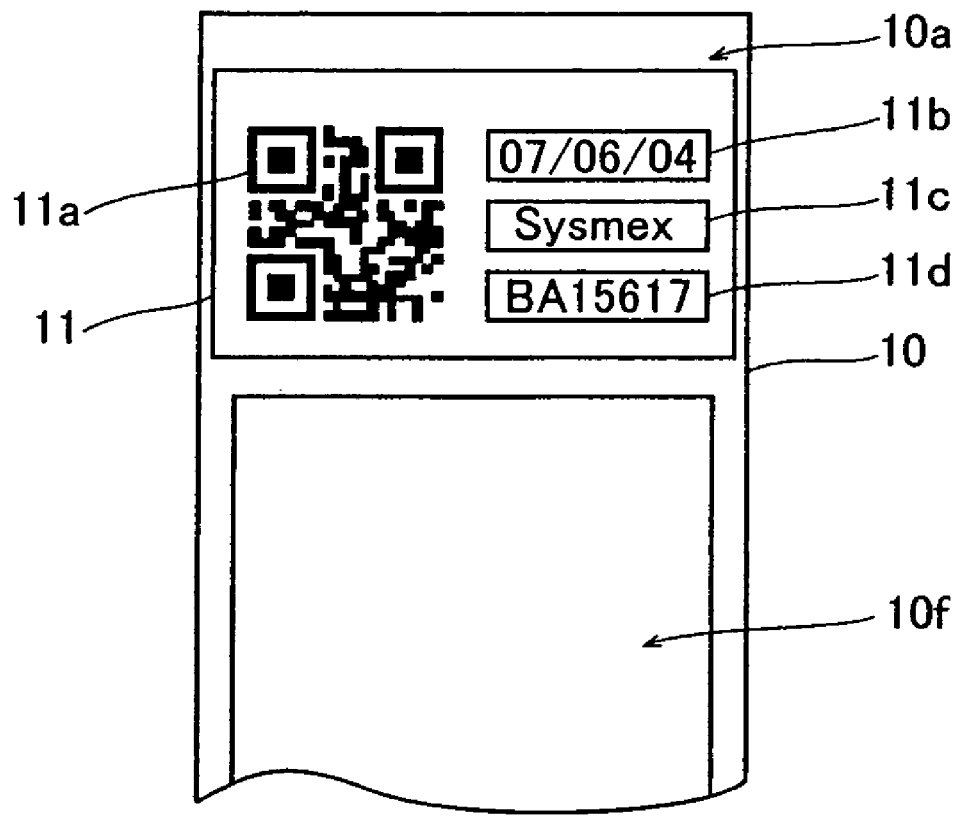
FIG. 21 is an enlarged view of a frosted part of a slide glass according to a third modification of the embodiment.

While the printable coating film 10g is formed on the region of the slide glass 10 corresponding to the frosted part 10a and the two-dimensional bar code 10b as well as the three rows of text data (10c to 10e) are printed on the upper surface of this coating film 10g in the aforementioned embodiment, the present invention is not restricted to this but the slide glass 10 may alternatively be constituted similarly to a slide glass 10 according to a third modification of the embodiment shown in FIG. 21. More specifically, a label 11 printed with a two-dimensional bar code 10a and three rows of text data (a date 11b, a name 11c and a sample number 11d) may be attached to a region of the slide glass 10 corresponding to a frosted part 10a, as shown in FIG. 21.

While the coating film provided on the region of the slide glass corresponding to the frosted part is formed to extend from the frosted part along the longitudinal direction of the slide glass for holding the specimen preparation area in the aforementioned embodiment, the present invention is not restricted to this but another coating film of a material different from that of the coating film provided on the region corresponding to the frosted part may alternatively be formed to extend from the frosted part along the longitudinal direction of the slide glass for holding the specimen preparation area.

While the two-dimensional bar code stores the specimen information such as the sample number, the date, the serial number and the name in the aforementioned embodiment, the present invention is not restricted to this but the two-dimensional bar code may alternatively store information selected from results of analysis measured in a blood analyzer and results of WBC (white blood cell), RBC (red blood cell), HGB (hemoglobin concentration), HCT (hematocrit), MCV (mean cell volume), MCH (mean cell hemoglobin), MCHC (mean cell hemoglobin concentration), PLT (number of platelets) and five types of white blood cells (neutrophil, eosinophil, basophil, monocyte and lymphocyte) as specimen information. According to the aforementioned embodiment, the two-dimensional bar code so stores the specimen information that the slide glass can hold a large quantity of information such as the aforementioned results of analysis. If the slide glass holds the aforementioned results of analysis, the operator can recognize the results of analysis made on a prescribed specimen prepared on a corresponding slide glass in addition to the specimen information such as the sample number by reading the two-dimensional bar code when reanalyzing the specimen after temporarily keeping the slide glass. Thus, the operator may not inquire the aforementioned results of analysis etc. from the host computer when reanalyzing the specimen prepared on the temporarily kept slide glass.

While the text data displayed on the frosted part of the slide glass are constituted of numerals and/or alphabetic characters in the aforementioned embodiment, the present invention is not restricted to this but the text data may alternatively be constituted of Chinese, hiragana and/or katakana characters in place of the numerals and/or alphabetic characters.

While the blood smear is prepared on the slide glass (specimen plate) in the aforementioned embodiment, the present invention is not restricted to this but a specimen for observing a urine visible component or a cytodiagnostic specimen for diagnosing metastasis of cancer cells may alternatively be prepared on the specimen plate. In this case, a specimen plate of resin such as acrylic resin, vinyl chloride resin or polycarbonate resin may alternatively be employed in place of the specimen plate of glass or quartz.

What is claimed is:

1. A stained blood smear preparation apparatus comprising:
    a stained specimen preparation part comprising a pipette for dispensing blood to a slide glass, a smearing part for preparing a blood smear of the blood on the slide glass, and a staining part for staining said blood smear, thereby providing a stained blood smear slide glass formed with a stained blood smear;
    a keeping part for storing a plurality of the stained blood smear slide glasses prepared in said stained specimen preparation part;

a transport part for transporting said stained blood smear slide glass to said keeping part or an external apparatus; and a control part that decides a destination of said stained blood smear slide glass from among said keeping part and said external apparatus and controls the transport part such that the transport part transports said stained blood smear to the destination, wherein said control part acquires specimen information from a computer communicably connected with said stained blood smear preparation apparatus for deciding a destination of said stained blood smear slide glass based on acquired specimen information and comprises a memory storing a blood smear preparation condition corresponding to said specimen information for selecting corresponding said blood smear preparation condition based on acquired specimen information and preparing said blood smear on said slide glass based on selected said blood smear preparation condition.

2. The stained blood smear preparation apparatus according to claim 1, wherein:

said external apparatus is either a blood smear analyzer for analyzing said stained blood smear on said stained blood smear slide glass or a feeder for supplying said stained blood smear slide glass to said blood smear analyzer.

3. The stained blood smear preparation apparatus according to claim 1, further comprising a printing part for printing said specimen information on a prescribed position of said slide glass.

4. The stained blood smear preparation apparatus according to claim 1, wherein:

said control part controls said stained specimen preparation part to prepare a stained blood smear slide glass for a visually observed blood smear based on a blood smear preparation condition for said visually observed blood smear and prepare a stained blood smear slide glass for an analyzed blood smear based on a blood smear preparation condition for said analyzed blood smear when said specimen information is comprises an instruction for preparing said visually observed blood smear and said analyzed blood smear.

5. The stained blood smear preparation apparatus according to claim 1, wherein the apparatus is configured for storing said stained blood smear slide glass in said keeping part and supplying said stained blood smear slide glass to said external apparatus in a state stored in a cassette.

6. The stained blood smear preparation apparatus according to claim 1, wherein the staining part includes a sucking/discharging part for supplying stain to the slide glass.

7. A stained blood smear preparation apparatus comprising:

a stained specimen preparation part comprising a pipette for dispensing blood to a slide glass, a smearing part for preparing a blood smear of the blood on the slide glass, and a staining part for staining said blood smear, thereby providing a stained blood smear slide glass formed with a stained blood smear;

a keeping part for storing a plurality of the stained blood smear slide glasses prepared in said stained specimen preparation part;

a transport part for transporting said stained blood smear slide glass to said keeping part or an external apparatus; and a control part that decides a destination of said stained blood smear slide glass from among said keeping part and said external apparatus and controls the transport part such that the transport part transports said stained blood smear to the destination, wherein said control part controls said stained blood smear preparation apparatus to supply said stained blood smear slide glass to said keeping part when said specimen information is comprises an instruction for preparing a visually observed blood smear, and supplies said stained blood smear slide glass to said external apparatus when said specimen information is comprises an instruction for preparing a blood smear for a blood smear analyzer.

8. A stained blood smear preparation apparatus to comprising:

a stained specimen preparation part comprising a pipette for dispensing blood to a slide glass, a smearing part for preparing a blood smear of the blood on the slide glass, and a staining part for staining said blood smear, thereby providing a stained blood smear slide glass formed with a stained blood smear;

a keeping part for storing a plurality of the stained blood smear slide glasses prepared in said stained specimen preparation part;

a transport part for transporting said stained blood smear slide glass to said keeping part or an external apparatus; and a control part that decides a destination of said stained blood smear slide glass from among said keeping part and said external apparatus and controls the transport part such that the transport part transports said stained blood smear to the destination, wherein the transport part comprises a transport mechanism mounted on a frame, a detection part arranged outside the frame, and a first transport path having an end adjacent to an entry port of the keeping part and a second transport path having an end adjacent to an inlet of the external apparatus.

9. A stained blood smear preparation apparatus comprising:

a stained specimen preparation part comprising a pipette for dispensing blood to a slide glass, a smearing part for preparing a blood smear of the blood on the slide glass, and a staining part for staining said blood smear, thereby providing a stained blood smear slide glass formed with a stained blood smear;

a keeping part for storing a plurality of the stained blood smear slide glasses prepared in said stained specimen preparation part;

a transport part for transporting said stained blood smear slide glass to said keeping part or an external apparatus; and a control part that decides a destination of said stained blood smear slide glass from among said keeping part and said external apparatus and controls the transport part such that the transport part transports said stained blood smear to the destination, wherein the keeping part comprises a feed part and a transport belt for moving the slide glass toward the keeping part, the slide glass having been transported to an entry port of the keeping part by the transport part.

* * * * *